US006248578B1

(12) United States Patent
Banerjee et al.

(10) Patent No.: US 6,248,578 B1
(45) Date of Patent: Jun. 19, 2001

(54) INFECTIOUS CLONE FOR HUMAN PARAINFLUENZA VIRUS TYPE 3

(75) Inventors: Amiya K. Banerjee, Moreland Hills; Michael A. Hoffman, Shaker Heights, both of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/073,492

(22) Filed: May 6, 1998

Related U.S. Application Data

(60) Provisional application No. 60/045,805, filed on May 7, 1997.

(51) Int. Cl.[7] .................................................... C12N 7/00
(52) U.S. Cl. ...................... 435/235.1; 435/471; 435/472; 435/475; 435/320.1; 536/23.72
(58) Field of Search ............................. 435/320.1, 235.1, 435/325, 472, 475, 471; 536/23.72

(56) References Cited

U.S. PATENT DOCUMENTS 5,578,473   11/1996   Palese et al. .
5,869,036 * 2/1999   Belshe et al. ........................ 424/93.2

FOREIGN PATENT DOCUMENTS 0 702 085 A1   7/1995   (EP) .

OTHER PUBLICATIONS

Stokes, A. et al. Virus Research 25: 91–103, 1992.*

Kingsbury, D.W. "Paramyxoviridae and Their Replication" in Fundamental Virology, 2nd edition, ed. B. N. Fields et al, Raven Press, NY, 1991.*

"Rescue of Synthetic Genomic RNA Analogs of Rabies Virus by Plasmid–Encoded Proteins" by Conzelmann, et al., Journal of Virology, vol. 68, No. 2. Feb. 1994, pp. 713–719.

"Rescue of measles viruses from cloned DNA" by Radecke, et al. The EMBO Journal, vol. 14, No. 23, Dec. 1995, pp. 5773–5784.

"A highly recombinogenic system for the recovery of infectious Sendai paramyxovirus from cDNA: generation of a novel copy–back nondefective interfering virus" by Garcin, et al. The EMBO Journal, vol. 14, No. 24, Dec. 1995, pp. 6087–6094.

"Efficient recovery of infectious vesicular stomatitis virus entirely from cDNA clones" by Whelan, et al., Proc. Natl. Acad. Sci. USA, Aug., 1995, pp. 9388–8392.

"Recombinant vesicular stomatitis viruses from DNA" by Lawson, et al., Proc. Natl. Acad. Sci. USA, vol. 92, May, 1995, pp. 4477–4481.

"Initiation of Sendai virus multiplication from transfected cDNA or RNA with negative or positive sense" by Kato, et al., Genes to Cells, (1996) 1, pp. 569–579.

"Recovery of Infectious Human Parainfluenza Virus Type 3 from CDNA" by Durbin, et al., Virology, vol. 235, Sep. 1997, pp. 323–332.

"An Infectious Clone of Human Parainfluenza Virus Type 3" by Hoffman, et al.,, Journal of Virology, vol. 71, No. 6, Jun., 1997, pp. 4272–4277.

Collins et al. Proceedings of the National Academy of Sciences USA 92:11563–11567, Dec. 5, 1997.*

* cited by examiner

Primary Examiner—Mary E. Mosher
(74) Attorney, Agent, or Firm—Calfee, Halter & Griswold LLP

(57) ABSTRACT

A system for generating recombinant, human parainfluenza virus, particularly infectious, recombinant, human parainfluenza virus type 3 (HPIV-3) is provided. In one embodiment, the system comprises a clone comprising a nucleotide sequence that encodes a full-length, positive sense, anti-genome of HPIV, and at least one support clone comprising a nucleotide sequence that encodes the HPIV P protein and the HPIV L protein. In another embodiment, the system further comprises a support clone which comprises a nucleotide sequence that encodes the HPIV NP protein. The present invention also provides a MAH clone which comprises a nucleotide sequence encoding the full-length, positive sense, anti-genome of HPIV-3. The clone also comprises an RNA polymerase promoter operatively linked to the HPIV-3 antigenome-encoding sequence. In a preferred embodiment, the clone further comprises a nucleotide sequence which encodes a ribozyme immediately downstream from the sequence encoding the HPIV-3 antigenome. The present invention also relates to a method of preparing recombinant HPIV-3 virus having site-specific mutations in the HPIV-3 genome. The method comprises preparing a clone comprising a modified HPIV-3 antigenome-encoding sequence; introducing the modified HPIV-3 clone and support clones which comprise nucleotide sequences encoding an HPIV-3 P protein, an HPIV-3 L protein, and, preferably, an HPIV-3 NP protein into host cells; and culturing the host cells under conditions that allow for synthesis of the modified HPIV-3 antigenome and the L, P, and NP proteins of HPIV-3.

29 Claims, 34 Drawing Sheets

```
                          DraI
          MboII            SwaI                                              DrdI
            |              ||                                                  |
ACCAAACAAGAGAAGAAACTTGTTGGGAAATATAAATTTAAATTAAAATTAACTTaggattaaagacattgactagaagg  80
TGGTTTGTTCTCTTCTTTGAACAAGCCTTTATATTTAAATTTAATTTTAATTGAAtcctaatttctgtaactgatcttcc
    •  |         •         ||   •         •         •         •    •|   •
      12                   36                                       71
                           37                                     BsaAI
                                                                    |
tcaagaaaagggaactctataatttcaaaaatgttgagcctatttgatacatttaatgcacgtaggcaagaaaacataac 160
agttcttttcccttgagatattaaagttttttacaactcggataaactatgtaaattacgtgcatccgttcttttgtattg
    •         •         •         •         •         •|        •         •
                                                       139

PvuII                                                         AvaII
      NspBII           EcoRII           BsmAI               StyI|
        |                |                |                   |
aaaatcagctggtggagctatcattcctggacagaaaaatactgtctccatatttgcccttggaccgacaataactgatg 240
ttttagtcgaccacctcgatagtaaggacctgtcttttatgacagaggtatataaacgggaacctggctgttattgactac
   •|         •         |         •    |         •    |        •|       •
     166                186              204           218               |
     166                                                                222
                      MboII
                      Ksp632I
                      EarI
                      SapI                                     NspI
                       |||                                       |
acaatgagaaaatgacattagctctttctatttctatctcattcactagataatgagaaacaacatgcacaaagggcaggg 320
tgttactcttttactgtaatcgagaagataaagatagagtaagtgatctattactctttgttgtacgtgtttcccgtccc
    •         •   •|||    •         •         •         •         |    •
                  261                                             302
                  262
                  262
                  263
ttcttggtgtctttattgtcaatggcttatgccaatccagagctttacctgacaacaaatggaagtaatgcagatgttaa 400
aagaaccacagaaataacagttaccgaatacggttaggtctcgaaatggactgttgtttaccttcattacgtctacaatt
    •         •         •         •         •         •         •         •

MsII            BglII
      |                |
atatgtcatatatatgattgagaaagatctaaaacggcaaaagtatggaggatttgtggttaagacgagagagatgatat 480
tatacagtatatatactaactcttttctagattttgccgttttcatacctcctaaacaccaattctgctctctctactata
   •|         •  |      •         •         •         •         •         •
    407          425
                          EcoRII         PstI
                 Tsp45I   EcoRII   EbvI         XmnI
                   | |      |        ||           |
atgaaaagacaactgagtggatatttggaagtgacctggattatgaccaggaaactatgctgcagaacggcagaaacaat 560
tactttctgttgactcacctataaaccttcactggacctaatactggtcctttgatacgacgtcttgccgtctttgtta
    •         •  |•| | •    | •         •|| •         |•
                 511 515    527           539          553
       Fig. 1a              540
```

```
                                                    SduI
                                                    SacI
       BglII                                        HgiAI              BglII
       MboII                                        |                  |
       | |
tcaacgattgaagatcttgttcacacatttgggtatccatcatgtttaggagctcttataatacagatctggatagtttt 640
agttgctaacttctagaacaagtgtgtaaacccataggtagtacaaatcctcgagaatattatgtctagacctatcaaaa
  | |         .         .         .         |         .         |         .
  570                                       610                 625
    572                                     610
                                            610
             SfaNI
             |
ggtcaaagccatcactagcatctcagggttaagaaaaggcttttcactcgattagaggctttcagacaagatggaacag 720
ccagtttcggtagtgatcgtagagtcccaattcttttccgaaaaagtgagctaatctccgaaagtctgttctaccttgtc
       .         |         .         .         .         .         .         .
                 658
                  Tsp45I                              HsmAI
                  HpbI                                Eco31I
                  AciI                                BsaI
    Cac8I         HsrBI                               AciI
    |             | | ||                              | ||
tgcaagcagggctggtattgagcggtgacacagtggatcagattgggtcaatcatgcggtctcaacagagcttggtaact 800
acgttcgtcccgaccataactcgccactgtgtcacctagtctaacccagttagtacgccagagttgtctcgaaccattga
    |         .         | | ||  .         .         .         | ||·        .
    722                 740                                    776
                          742                                   778
                            744                                  778
                             745                                  779
              VspI
              AseI
      BsmAI
      |       | |
cttatggttgagacattaataacaatgaatactagcagaaatgaccctcacaaccatagaaaagaatatacaaattgttgg 880
gaataccaactctgtaattattgttacttatgatcgtctttactggagtgttggtatattttcttatatgtttaacaacc
      |       | |         .         .         .         .         .         .
      810     815
                 815
              BspMI
      SfaNI                   MboII                          BsmAI    BbvI    PleI
      | |                     |                              |        |       |
taactacataagagatgcaggtcttgcttcattcttcaatacaatcaggtatggaattgagactagaatggcagatttga 960
attgatgtattctatacgtccagaacgaagtaagaagttatgttagtccataccttaactctgatcttaccgtagaaact
      | |         .         |         .         .         |·        ·|       |·
      894                   913                            939       951     959
       897
      EcoRV                                      AvaII
      |                                          |
ctctatctactctcagaccagatatcaatagattaaaagctctgatggaattgtatttatcaaagggaccacgcgctcct 1040
gagatagatgagagtctggtctatagttatctaattttcgagactaccttaacataaatagtttccctggtgcgcgagga
      .         .         ·|        .         .         .         |         .
                           981                                    1026
```

*Fig. 1b*

```
                          HphI              EcoRII          NdaI          BarIII
                           |                  |              |              |
tttatctgtatcctcagagatcctatacatggtgagttcgcaccaggcaactatcctgccatatggagttatgcaatggg  1120
aaatagacataggagtctctaggatatgtaccactcaagcgtggtccgttgataggacggtatacctcaatacgttaccc
     •      |    •     |     •     |       •     |     •      •
           1071       1083        1100         1113

PvuII
    Bsp1407I                      Tsp45I MboII     XbaI                    NspBII
       |                             |     |        |                       |
ggtggcagttgtacaaaacagagccatgcaacagtatgtgacgggaagatcatatctagatattgatatgttccagctgg  1200
ccaccgtcaacatgttttgtctcggtacgttgtcatacactgccccttctagtatagatctataactatacaaggtcgacc
 |       •     •     |     •      |  •  |   •     |     •     •  |
1130                1158        1165      1175                  1194
                                                                1194
                 SduI
        SfaNI    SacI            McoII
    PmlI         HgiAI   BsrI
    BsaAI  Eco57I   |     |              Tsp45I
      |      |      |     |                |
gacaagcagtagcacgtgatgctgaagctcagatgagctcaacactggaagatgaacttggagtgacacacgaagccaaa  1280
ctgttcgtcatcgtgcactacgacttcgagtctactcgagttgtgaccttctacttgaacctcactgtgtgcttcggttt
  |      |   •     |     •      |     •    |   •     •     |      •     •
 1213   1222      1235         1244         1263
 1213             1235         1248
        1218      1235

MslI
    HindIII                      BsmAI               AciI             BstXI
       |                            |                  |              ||
gaaagcttgaaaagacatataaggaacataaacagttcagagacatctttccacaaaccaacaggcggatcagccataga  1360
cttttcgaactttttctgtatattccttgtatttgtcaagtctctgtagaaaggtgtttggttgtccgcctagtcggtatct
  |      •     •     •     |     •      •     |     •      •  |     ||
1283                     1320                              1345   1354
      SapI                                                        1355
      MboII
      Ksp632I
         |
gatggcaatagatgaagaaccagaacaatttgaacacagagcagatcaagaacaagatggagaacctcaatcatctataa  1440
ctaccgttatctacttcttcggtcttgttaaacttgtgtctcgtctagttcttgttctacctcttggagttagtagatatt
  •      |     •     •     •     •      •     •     •     •      •     •    •
        1374
        1374
        1374
                                            AvaII
                                            RsrII  Cac8I
                                             ||     |
tccaatatgcttgggcagaaggaaacagaagtgatgatcggaccgagcaagctacagaatccgacaatatcaagactgaa  1520
aggttatacgaacccgtcttcctttgtcttcactactagcctggctcgttcgatgtcttaggctgttatagttctgactt
  •      •     •     •     •       ||    |     •     •      •     •     •
                                  1479  1487
                                  1480

Fig. 1c
```

```
                                    PleI                                          FokI
           BsmAI                    BsmAI         MboII         HindII
             |                       | |            |             |  |
   caacaaaacatcagagacagactaaacaagagactcaacgacaagaagaaacaaggcagtcaaccatccaccaatcccac  1600
   gttgttttgtagtctctgtctgatttgttctctgagttgctgttcttctttgttccgtcagttggtaggtggttagggtg
   .         |         .         | |.         |         .         |.        |
            1534                1550          1565                1579
                                 1552                             1585
                                                                  HindII
           EcoRII                                            FlaI          BsaBI
             |                                                | |            |
   aaacagaacgaaccaggacgaaatagacgatctgttcaatgcatttggaagcaactaactgagtcaacattttgatctaa  1680
   tttgtcttgcttggtcctgctttatctgtcagacaagttacgtaaaccttcgttgattgactcagttgtaaaactagatt
   .         |         .         .         .         .       |        |   .
            1613                                            1661       1674
                                                            1663
                                                                      PleI   Cac8I
              NP Gene End     P Gene Start                              |     |
   atcaat aataaataagaaaaac tt aggattaaag atcctatcataccagaacatagagtggtaaatttagagtctgctt  1760
   tagttattatttattcttttt gaatcctaatttcttaggatagtatggtcttgtatctcaccatttaaatctcagacgaa
   .         .         .         .         .         .         .       .| |
                                                                       1751 1757
                                                                           MboII
                         SfaNI                                             Ksp6321
                           |                                                 |
   gcaactcaatcaatagagagttc atcg aaaagcgatgctaaaaactatcaaatcatggattcttgggaagaggaaccaaga  1840
   cgttgagttagttatctctcaactacctttcgctacgattttttgatagtttagtacctaagaacccttctccttggttct
   .         .         .         .         .         .         .         . |
                                  1793                                      1826
                                                                            1826
                                                                      MboII
           BsaRI                   EcoRI                              Bbal
             |                       |                                  |
   gataaatcaactaatatctcctcggccctcaacatcattgaattcatactcagcaccgaccccaagaagacctatcgga  1920
   ctatttagttgattatagaggagccgggagttgtagtaacttaagtatgagtcgtggctgggggttcttctggatagcct
   .         .         |         .   t     .         .         .         . |
                      1858               1880                              1907
                                                                           1907
                               HaeII      HindII
                                 |          |
   aaacgacacaatcaacacaagaacccagcaactcagcgccaccatctgtcaaccagaaatcaaaccaacagaaacaagtg  2000
   tttgctgtgttagttgtgttcttgggtcgttgagtcgcggtggtagacagttggtctttagtttggttgtctttgttcac
   .         .         .        |          |       .         .         .
                                1955       1968
                                              MsII    Bsp1407I                SspI
                                                |        |                      |
   aaaaagttagtggatcaactgacaaaaatagacagtctgggtcatcacacgaatgtacaacagaagcaaaagatagaaat  2080
   ttttcaatcacctagttgactgttttatctgtcagacccagtagtgtgcttacatgttgtcttcgttttctatcttta
   .         .         .         .         .         .|  |   .         .       |.
                                                     2046 12054                2078
                Fig. 1d
```

```
                                                                    GsuI
                                                                   EcoBII
                                              HbvI         PshAI   BsmAI
   BclI       Bsp1407I          MboII          |           BsmAI   BsAI
    |             |               |   |         |            | |    ||   |
attgatcaggaaactgtacagggaggatctgggagaagaagcagctcagatagtagagctgagactgtggtctctggagg  2160
taactagtcctttgacatgtccctcctagaccctcttcttcgtcgagtctatcatctcgactctgacaccagagacctcc
  |           |                    |     •|              • || •  ||    |   •
 2083        2095                 2115                    2141  2149
                                      2121                  2143   2150
                                                                  2149
                                                                       2154

SfaNI                                SspI
            |                                   |
aatctctggaagcatcacagattctaaaaatggaacccaaaacacggagaatatttgatctcaatgaaattagaaagatgg  2240
ttagagaccttcgtagtgtctaagattttttaccttgggttttgtgcctcttataactagagttactttaatctttctacc
   •        |           •    •       •             |       •    •   •    •
           2173                                   2210
   PlaI                        PstI           EcoRV
    |                           |               |
ataaggactctattgagaggaaaatgcgacaatctgcagatgttccaagcgagatatcaggaagtgatgtcatatttaca  2320
tattcctgagataactctccttttacgctgttagacgtctacaaggttcgctctatagtccttcactacagtataaatgt
    |                  •        |         •       |              •     •
   2246                        2274             2293
                          HindIII
              BclI         MboII
                |          |   |
acagaacaaagtagaaacagtgatcatggaagaagcttggaacctatcagtacacctgatacaagttcaatgagtgttgt  2400
tgtcttgtttcatctttgtcactagtaccttcttcgaaccttggatagtcatgtggactatgttctagttactcacaaca
       •        •       •|         |•  |            •      •            •      •
              2341      2349
                           2353

MboII                 MboII
         BbvI              MboII         FokI   MboII           MboII       MboII
          |                 |  |           |     |                |           |
tactgctgcgacaccagatgatgaagaagaaatactaatgaaaaatagtaggatgaagaaaagttcttcaacacaccaag  2480
atgacgacgctgtggtctactacttcttctttatgattactttttatcatcctacttcttttcaagaagttgtgtggttc
    |             •         |  | •                |    |  •            |        |
   2405                    2423                   2451                 2465     2480
                            2426          BsrI   2455
                                           |
aagatgacaaaagaattaaaaaagggggggggggaaaagggaaagactggtttaagaaatcaagagatactgacaaccag  2560
ttctactgttttcttaatttttttccccccccccccttttcccttctgaccaaattctttagttctctatgactgttggtc
    •       •         •              •   |        •                •           •
                                        2526
acatcaacatcagatcacaaacccacatcaaaagggcaaaagaaaatctcaaaaacaacaaccaccaacaccgacacaaa  2640
tgtagttgtagtctagtgtttgggtgtagttttcccgttttcttttagagttttgttgttggcggttgtggctgtgttt
```

Fig. 1e

```
ggggcaaacagaaacacagacagaatcatcagaaacacaatccccatcatggaatcccattatcgacaacaacactgacc  2720
ccccgtttgtctttgtgtctgtcttagtagtctttgtgttagggtagtaccttagggtaatagctgttgttgttactgg gaaccgaacagacaagcacaaccccccaacaacaactcccagatcaactcgtacaaaagaatcaatccgaacaaactct  2800
cttggcttgtctgttcgtgttggggggttgttgttgagggtctagttgagcatgttttcttagttaggcttgtttgaga
```
                                    MboII
                   Mfal             Ksp632I   ClaI
                    |                 |        |
```
gaatccaaacccaagacacaaaagacaattggaaaggaaaggaaggatacagaagagagcaatcgatttacagagagggc  2880
cttaggtttgggttctgtgtttctgttaacctttcctttccttcctatgtcttctctcgttagctaaatgtctctcccg
                    |                        |         |
                  2826                     2852       2862
                                           2852
                                          BsaBI
                                            |
aattactctattgcagaatcttggtgtaattcaatctacactaaaactagatttatatcaagacaaacgagttgtatgtg  2960
ttaatgagataacgtcttagaaccacattaagttagatgtagttttgatctaaatatagttctgtttgctcaacatacac
                                           |
                                         2930
    SfaNI
      |
tagcaaatgtactaaacaatgtagatactgcatcaaagatagacttcctagcaggattaggcataggggtttcaatggac  3040
atcgtttacatgatttgttacatctatgacgtagtttctatctgaaggatcgtcctaatcagtatccccaaagttacctg
      |
    2990
 VspI
 AsaI                             BglII                                     MboII
   |                                |                                         |
aatgacacaaaattaatacagatacaaaatgaaatgttaaacctcaaagcagatctaaagagaatggacgaatcacatag  3120
ttactgtgttttaattatgtctatgttttactttacaatttggagtttcgtctagatttctcttacctgcttagtgtatc
   |                                |                                         |
 3052                              3091                                     3120
 3052
                        BclI                                              BsaRI
                          |                                                 |
aagattgatagaaaatcaaagagaacaactgtcattgatcacatcgttaatttcaaatcttaaaattatgactgagagag  3200
ttctaactatcttttagtttctcttgttgacagtaactagtgtagcaattaaagtttagaattttaatactgactctctc
                          |                                                 |
                        3156                                              3198
             BclI           MboII
               |              |
gaggaaagaaagaccaaaatgaatccaatgagagagtatctatgatcaagacaaaattgaaagaagaaaagatcaagaaa  3280
ctcctttctttctggttttacttaggttactctctcatagatactagttctgtttaactttcttcttttctagttcttt
               |              |
             3243           3263
```

*Fig. 1f*

```
                                    BclI                    MboII
                                     |                       |
gaggaaagaaagaccaaaatgaatccaatgagagagtatctatgatcaagacaaaattgaaagaagaaaagatcaagaaa  3280
ctcctttctttctggttttacttaggttactctctcatagatactagttctgttttaacttttcttcttttctagttcttt
                             .        .           .         .           .
                                    3243                    3263
 EcoRII                                   BsaBI      NspI
 SexAI                                      |         |
  ||
accaggtttgacccacttatggaggcacaaggtattgacaagaatatacctgatctatatcgacatgcaggaaatacgtt   3360
tggtccaaactgggtgaatacctccgtgttccataactgttcttatatggactagatatagctgtacgtcctttatgcaa
 ||                                        |         |
 3281                                    3332      3343
  3282
                                 PlaI
                                 BcgI
                                 ||
agagaacgacgtacaagttaaatcagagatattaagttcatacaacgagtcaaatgcaacaagactaatactcagaaaag  3440
tctcttgttgcatgttcaatttagtctctataattcaagtatgttgctcagtttacgttgttctgattatgggtcttttc
                                 ||
                                 3406
                                  3407
     SpeI
      |
tgagcagtacaatgagatcactagttgcagtcatcaacaacagcaatctcccacaaagcagaaaacaatcatatataaac   3520
actcgtcatgttactctagtgatcaacgtcagtagttgttgtcgttagagggtgtttcgtcttttgttagtatatatttg
      |
     3460
                                                              HpaI
                                          NspI                HindII
                                          AflIII      MboII   MfeI
   BsaDI        MboII                       |           |      |   P stop
     |           |
gaactcaaacattgcaaaagtgatgaagaagtatctgaattgatggacatgttcaatgaagatgttaacaattgctaatag   3600
cttgagtttgtaacgttttcactacttcttcatagacttaactacctgtacaagttacttctacaattgttaacgatttc
     |           |                          |           |      |      |
    3530        3545                       3567        3578   3589
                                           3567                3584
                                                                3584 atcaaataaaaaaaacaacaccgaataaatagacaacaaacaacagtagatcaaaacctatcaacacacacaaaatcaag   3680
tagtttattttttttgttgtggcttatttatctgttcttgttgtcatctagttttggatagttgtgtggtgtttagttc VspI
                                                                   AsaI
                                  P end        M start              |
cagagtgaaacaatagacatcaatcaatatacaaataagaaaaatttgggattaaagaataaattaatccttgtccaaaa   3760
gtctcactttgttatctgtagttagttatatgtttattcttttaaatcctaatttcttatttaattaggaacaggtttt
                                                                   |
                                                                  3743
                                                                   3743
```

*Fig. 1g*

```
                                    PlaI
                                     |
tgagtataactaactctgcaatatacacattcccggagtcatcattctctgagaatggtcatatagaaccattaccactc  3840
actcatattgattgagacgttatatgtgtaagggcctcagtagtaagagactcttaccagtatatcttggtaatggtgag
                                     |
                                    3796
                                                              PflMI      BamHI
                                                               |           |
aaagtcaatgaacagagaaaagcagtacctcacattagagttgccaaaatcggaaatccaccaaaacatggatcccggta  3920
tttcagttacttgtctcttttcgtcatggagtgtaatctcaacggttttagcctttaggtggttttgtacctagggccat
                                                               |         |
                                                              3901      3910

MboII
  FokI    MboII                                                           Tsp45I
   | |     |                                                                |
tttggatgtcttcttactcggcttcttcgagatgggaacgaatcaaagacaaatacgggagtgtgaatgatcttgacagtg  4000
aaacctacagaagaatgagccgaagaagctctaccttgcttagtttctgtttatgccctcacacttactagaactgtcac
   | |*    |                                                                | .
  3924     3944                                                            3998
     3929

SmaI
 AvaI                                                  BarI        EcoRII
  |                                                     |            |
acccgggttacaaagtttgtggctctggatcattaccaatcggattagccaaatacactgggaatgaccaggaattatta  4080
tgggcccaatgtttcaaacaccgagacctagtaatggttagcctaatcggtttatgtgacctttactggtccttaataat
  |                                                     |            |
4002                                                   4057         4068
4002
      BsrI  MsII    MboII
       |     |       |
caactaaactggacatagaagtgagaagaacagtcaaagcgaaagaaatgattgtttatacggtacaaaatataaaacca  4160
gttgatttgacctgtatcttcactcttcttgtcagtttcgctttctttactaacaaatatgccatgttttatattttggt
       |     |       |
     4088  4094    4105
             AvaII
   StyI
   NcoI         AccI
   DsaI    BsrI                        SfaNI          MfaI         DraI
   | | |    |                           |             |            |
gaactgtacccatggtccagtagactaagaaaaggaatgttgttcgatgccaacaaagttgctcttgctcctcaatgtct  4240
cttgacatgggtaccaggtcatctgattcttttcctacaacaagctacggttgttcaacgagaacgaggagttacaga
   | | |    |                           |             |            |
  4170 4177                           4206          4228         4238
  4170    4180
  4170
       4174
```

*Fig. 1h*

```
                              MboII           MfaI              DraI
                                |               |                 |
tccactagataggagcataaaattcagagtaatcttcgttaattgtacggcaattggatcaataaccttgtttaaaattc   4320
aggtgatctatcctcgtatttttaagtctcattagaagcaattaacatgccgttaacctagttattggaacaaattttaag
       .         .         .   |    .   |    .         .   |    .         .
                              4273     4291              4311
                                              BspMI
                                              PstI
  BstXI      SfaNI                              | |
    |          |                                | |
ccaagtcaatggcatcactatctctacccagcacaatatcaatcaatctgcaggtacacatcaaaacaggggttcagact   4400
ggttcagttaccgtagtgatagagatgggtcgtgttatagttagttagacgtccatgtgtagttttgtccccaagtctga
|    .    |    .         .         .         .| |   .         .         .         .
4321     4332                                4368
                                              4370
                 FokI      HphI                      AvaII         BclI
                   |         |                         |             |
gattctaaagggatagttcaaattttggatgagaagggtgaaaaatcactgaatttcatggtccatctcggattgatcaa   4480
ctaagatttccctatcaagtttaaaacctactcttcccacttttagtgacttaaagtaccaggtagagcctaactagtt
         .    |    .|    .         .         .       . |   .         .|    .
              4427   4437                              4460          4474
       ScaI
         |
aagaaaagtaggcagaatgtactctgtcgagtactgtaaacagaaaatcgagaaaatgagattgatattttctttgggat   4560
ttcttttcatccgtcttacatgagacagctcatgacatttgtcttttagctcttttactctaactataaaagaaaccta
         .         | .         .         .         .         .         .         .
                  4510
              MsII          BsaBI                         PvuII
      MboII    |     BsrI    |                            NspBII
        |      |      |      |                              |
tagttggaggaatcagtcttcatgtcaatgcaactgatctatatcaaaaacactagcaactcagctggtattcaaaagg    4640
atcaacctccttagtcagaagtacagttacgttgacctagatatagttttgtgatcgttcagtcgaccataagttttcc
         .  |  .|    .  |   .|    .         .         .         .|    .         .
          4577  4581    4593                                     4623
                        4597                                     4623
        BsaBI
         |
gagatttgttatcccttaatggatctaaatccacatctcaatctagttatctgggcttcatcagtagagattacaagagt   4720
ctctaaacaatagggaattacctagatttaggtgtagagttagatcaatagacccgaagtagtcatctctaatgttctca
         .    |    .         .         .         .         .         .         .
              4662
   SfaNI
   FokI              EcoRII
    ||                  |
ggatgcaattttccaaccttctttacctggcgagttcagatactatcctaacattattgcaaaaggagttgggaaaatca   4800
cctacgttaaaaggttggaagaaatgaaccgctcaagtctatgataggattgtaataacgttttcctcaacccttttagt
||       .         | .         .         .         .         .         .         .
4721              4745
4722
                                                    Fig. 1i
```

```
                SpeI
                 |                                                    M end
aacaatggaactagtaatctctatttttgatctggatatatctattaagccaaagcaaataagaga|aatcaaaaa|cttag  4880
ttgttaccttgatcattagagataaaactagacctatatagataattcggtttcgtttattctct|ttagttttt|gaatc
          |
         4810
                                   BbvI
                                    |                                         MboII
 F start             F               |                                         |
|gacaaaag|aagtcaataccaacaactattagcagccacactcgctggaacaagaaagaagggataaaaaaagtttaacag  4960
|ctgttttc|ttcagttatggttgttgataatcgtcggtgtgagcgaccttgttctttcttccctattttttttcaaattgtc
                            |                                                  |
                           4911                                              4960 aagaaacaaaaacaaaaagcagagaacaccagaacaacaagatcaaaacacccaacccactcaaaacgaaaatctcaaaa  5040
ttctttgttttttgttttcgtgtcttgtggtcttgttgttctagttttgtgggttgggtgagttttgcttttagagtttt MsII
                                              BstXI        SfaNI
                                              ||             |
gagattggcaacacaacaaacactgaacat|atg|ccaacctcaatactgctaattattacaaccatgattatggcatctt  5120
ctctaaccgttgtgttgtttgtgacttgtagtacggttggagttatgacgattaataatgttggtactaataccgtagaa
                                                            ||         |
                                                           5103       5114
                                                            5104

MsII           HpaI        MboII
             EcoRV         NspI           HindII      FokI    EcoRV
              |             ||              |          |       |
tctgccaaatagatatcacaaaactacagcatgtaggtgtattggttaacagtcccaaagggatgaagatatcacaaaac  5200
agacggtttatctatagtgttttgatgtcgtacatccacataaccaattgtcagggtttccctacttctatagtgttttg
              |             ||              |         |        |  |
             5132          5149           5165       5181      5188
                           5150           5165                 5185

EcoRV                     MboII              Tsp45I
              |                         |                 HphI
              |                         |                  ||
tttgaaacaagatatcatatttttgagcctcataccaaaaatagaagattctaactcttgtggtgaccaacagatcaagca  5280
aaactttgttctatagattaaaactcggagtatggttttatcttctaagattgagaacaccactggttgtctagttcgt
              |                         |                  ||
             5211                      5243               5261
                                                          5262

BclI                              FokI
                   |                                 |
atacaagaggttattggatagactgatcattcctttatatgatggattaagattacagaaggatgtgatagtgtccaatc  5360
tatgttctccaataacctatctgactagtaaggaaatatactacctaattctaatgtcttcctacactatcacaggttag
                   |                                 |
                  5304                              5341
```

*Fig. 1j*

```
aagaatccaatgaaaacactgaccccagaacaaaacgattctttggaggggtaattggaactattgctctgggagtggca   5440
ttcttaggttacttttgtgactggggtcttgttttgctaagaaacctccccattaaccttgataacgagaccctcaccgt
```

```
                    AciI                            CacBI
                    NspBII              BglI
                    | |                 |           |
acctcagcacaaattacagcggcagttgctctggttgaagccaagcaggcaagatcagacattgaaaaactcaaggaagc   5520
tggagtcgtgtttaatgtcgccgtcaacgagaccaagttcggttcgtccgttctagtctgtaacttttttgagttccttcg
                    | |                 |           |
                    5457                5480
                       5459                 5485
```

```
                              SduI
                              SacI                                    EcoRII
                BsgI          HgiAI              BcgI         AvaII
                |             |                  |            | |
aatcagggacacaaacaaagcagtgcagtcagtccagagctccataggaaatttgatagtagcaattaaatcggtccagg   5600
ttagtccctgtgtttgtttcgtcacgtcagtcaggtctcgaggtatcctttaaactatcatcgttaatttagccaggtcc
                |             |                  |            | |
                5543          5557               5582         5593
                              5557                                 5596
                              5557
```

```
    HindII                MfeI                    BbvI    Eco57I
    |                     |                       |       |
attatgtcaacaaagaaatcgtgccatcaattgcgagattaggttgtgaagcagcaggacttcagttaggaattgcatta   5680
taatacagttgttccttttagcacggtagttaacgctctaatccaacacttcgtcgtcctgaagtcaatccttaacgtaat
    |                     |                        |     |
    5606                  5628                    5651   5660
                          HphI
                          |
acacagcattactcagaattaacaaacatatttcggtgataacataggatcattacaagaaaaagggataaaattacaagg   5760
tgtgtcgtaatgagtcttaattgtttgtataagccactattgtatcctagtaatgttctttttccctatttaatgttcc
                          |
                          5714
```

```
SfaNI      AciI
|          |
tatagcatcattataccgcacaaatatcacagagatattcacaacatcaacagttgataaatatgatatttatgatctat   5840
atatcgtagtaatatggcgtgtttatagtgtctctataagtgttgtagttgtcaactatttatactataaatactagata
|          |
5765       5776
                HphI               HindII              HphI         PlaI
                |                  |                   |            |
tatttacagaatcaataaaggtgagagttatagatgttgacttgaatgattactcaatcaccctccaagtcagactccct   5920
ataaatgtcttagttatttccactctcaatatctacaactgaacttactaatgagttagtgggaggttcagtctgaggga
                |                  |                   |            |
                5860               5876                5898         5913
```

*Fig. 1k*

```
                                                                       FokI
                                                                        |
ttattaactagactgctgaacacccagatttacagagtagattccatatcctataacatccaaaacagagaatggtatat   6000
aataattgatctgacgacttgtgggtctaaatgtctcatctaaggtatagtatattgtaggttttgtctcttaccatata
                                                                    |
                                                                   5977

MboII
  Ksp632I
  EarI            BspHI                                              BsmI
  ||               |                                                  |
ccctcttcccagccacatcatgacaaaaggggcatttctaggtggagcagatgtcaaagaatgtatagaagcattcagca   6080
gggagaagggtcggtgtagtactgttttccccgtaaagatccacctcgtctacagtttcttacatatcttcgtaagtcgt
  ||              |                                                  •|
  6003            6018                                              6071
  6003
   6004

EcoRII           PfIMI
                    |                |
gttatatatgcccttctgatccaggatttgtactaaaccatgaaatggagagctgtttatcaggaaacatatcccaatgt   6160
caatatatacgggaagactaggtcctaaacatgatttggtactttacctctcgacaaatagtcctttgtatagggttaca
                    |                |
                  6101             6118

DsaI                                          EBseRI
       |                                              |
ccaagaaccgtggttaaatcagacattgttccaagatatgcatttgtcaatggaggagtggttgcaaattgtataacaac   6240
ggttcttggcaccaatttagtctgtaacaaggttctatacgtaaacagttacctcctcaccaacgtttaacatattgttg
       |                                              |
      6168                                          6213

Bsp1407I
      MsII
      NspI  NspI                              BcII
      AflIII  BcgI                            EcoNI
      || | |    |                              | |
cacatgtacatgcaacggtatcggtaatagaatcaatcaaccacctgatcaaggagtaaaaattataacacataaagaat   6320
gtgtacatgtacgttgccatagccattatcttcgttagttggtggactagttcctcattttaatattgtgtatttctta
      || | |    |                              | |
      6242    6252                           6284
      6242 6248                              6286
        6243
          6245

BsmI
                    |
gtaatacaataggtatcaacggaatgctgttcaatacaaataaagaaggaactcttgcatttacacaccaaatgatata   6400
cattatgttatccatagttgccttacgacaagttatgtttatttcttccttgagaacgtaaaatgtgtggtttactatat
                    |
                  6342
```

Fig. 1l

```
                                    SduI                          MboII
                                    SacI                    XbaI  PleI
                  MfeI              HgiAI             BglII       Ksp632I
                   |                  |                 |    |     |  |
acattaaacaattctgttgcactagatccaattgacatatcaatcgagctcaataaggccaaatcagatctagaagagtc  6480
tgtaatttgttaagacaacgtgaactaggtttactgtatagttagctcgagttattccggtttagtctagatcttctcag
                   |                  |                 |    |     |  |
                  6429               6446              6446  6473
                                     6446              6449  6476
                                     6446                    6473

SfaNI
                                              |
aaaagaatggataagaaggtcaaatcaaaaactagattccattggaaaattggcatcaacttagcaccacaatcataattg  6560
ttttcttacctattcttccagtttagttttttgatctaaggtaacctttaaccgtagttagatcgtggtgttagtattaac
                                              |
                                             6532

VspI
                      AseI                                              EcoRI
                       |                                                  |
ttttgataatgataattatattgtttataattaatgtaacgataattataattgcagttaagtattacagaattcaaaag  6640
aaaactattactattaatataacaaatattaattacattgctattaatattaacgtcaattcataatgtcttaagttttc
                       |                                                  |
                      6590                                               6630
                      6590

NdeI                    BglII
                           |                        |
agaaatcgagtggatcaaaatgataaaccatatgtattaacaaacaaatgacagatctatagatcattagatattaa aat  6720
tctttagctcacctagttttactatttggtatacataattgtttgtttactgtctagatatctagtaatctataatt tta
                           |                        |                         XcmI
                          6669      HN             6693                         |
  F end    HN start
 tataaaaaa ctt aggagtaaag ttacgcaattcaactctactcatataattgagaaagaacccaacagacaaatccaaat  6800
 atatttttt gaa tcctcatttc aatgcgttaagttgagatgagtatattaacactttcttggggttgtctgtttaggttta
                                                                              |
                                                                             6795
                                                           StyI
                                                           NcoI
                                                           DsaI
         BsrI                     SfaNI              FokI
          |                         |                 | |
ccgag atg gaatacaggaagcacaccaatcacgggaaagatgctggtaatgagctggaaacatccatggctactcatggc  6880
ggctc tac cttatgaccttcgtgtggttagtgcccttctacgaccattactcgaccttgtaggtaccgatgagtaccg
          |                         |                 | |
         6813                      6839              6861
```

Fig. 1m

```
                                                                6864
                                                                6864
                                                                6864
                                                                   MsII
         HphI                              EcoRII           MboII
          |                                  |                |  |
aacaagatcaccaacaagataacatatatattatggacaataatcctggtgttattatcaatagtcttcatcatagtgct  6960
ttgttctagtggttgttctattgtatatataatacctgttattaggaccacaataatagttatcagaagtagtatcacga
 |                                           |                |  |·
 6888                                       6925             6945
VspI                                                              6949
AseI                       BsrDI
 |                           |
aattaattccatcaaaagtgaaaaagcccatgaactattgctacaagacgtaaacaatgagtttatggaagttacagaaa  7040
ttaattaaggtagttttcacttttcgggtacttagtaacgatgttctgcatttgttactcaaatacctttcaatgtcttt
 |                            |                                             
 6962                        6996
 6962
                          VspI
                          AseI
        SfaNI     SspI                                              PlaI
          |        | |                                                |
agatccaaatggcatcggataatatattaatgatctaatacagtcaggagtgaatacaaggcttcttacaattcagagtcat 7120
tctaggtttaccgtagcctattataattactagattatgtcagtcctcacttatgttccgaagaatgttaagtctcagta
           ·|     ·| |                                              |      ·
          7052    7061                                             7114
                   7064
                   7064
        EcoRV
          |
gtccagaattatataccgatatcattgacacaacaaatgtcggatcttaggaaattcattagtgaaattacaattaggaa  7200
caggtcttaatatatggctatagtaactgtgttgtttacagcctagaatcctttaagtaatcactttaatgttaatcctt
           |·
          7138
                                CacBI
                                AciI
                                SfaNI         DraI    MXcmI          SfaNI
                                  | |          |        |              |
tgataatcgagaagtgcctccacaaagaataacacatgatgcgggcataaaacctttaaatccagatgattttggagat  7280
actattagctcttcacggaggtgtttcttattgtgtactacgcccgtattttggaaatttaggtctactaaaaacctcta
                                ·| |          |  ·     |  ·            |·
                                7238          7255    7262            7278
                                 7241
                                 7241
        MboII
          |
gcacgtctggtcttccatctttaatgaaaactccaaaaataagtttaatgccggggccgggattattagctatgccaacg  7360
cgtgcagaccagaaggtagaaattacttttgaggttttattccaattacggccccggccctaataatcgatacggttgc
           ·|
          7291
                                            Fig. 1n
```

```
                                                                                          XhoI
                                                                                          AvaI
                                                                                            |
actgttgatggctgtgttagaactccgtccttagttataaatgatctgatttatgcttatacctcaaatctaattactag  7440
tgacaactaccgacacaatcttgaggcaggaatcaatatttactagactaaatacgaatatggagtttagattaatgagc
                                                                                            |
                                                                                          7437
                                                                                          7437

KpnI
                                                                            BanI
        EcoRII                                                                |
          |
aggttgccaggatataggaaaatcatatcaagtattacagatagggataataactgtaaactcagacttggtacctgact  7520
tccaacggtcctatatccttttagtatagttcataatgtctatccctattattgacatttgagtctgaaccatggactga
  |                                                                           |
 7447                                                                        7510
                                                                             7510

StyI
        AvrII                                                                        BsaBI
          |                                                                            |
taaatcctaggatctctcatcctttcaacataaatgacaatagaaagtcatgttctctagcactcctaaacacagatgta  7600
atttaggatcctagagagtatgaaagttgtatttactgttatctttcagtacaagagatcgtgaggatttgtgtctacat
  |                                                                                    |
 7526                                                                                7595
 7526
                PleI                            SfaNI         MboII          EcoRV
                  |                               |             |              |
tatcaactgtgttcgactcccaaagttgatgaaagatcagattatgcatcatcaggcatagaagatattgtacttgatat  7680
atagttgacacaagctgagggtttcaactactttctagtctaatacgtagtagtccgtatcttctataacatgaactata
                  |                               |             |              |
                7615                            7646          7661           7676
                                                                              AciI
        BspHI                                                        BclI  NdeI  |
          |                                                           |     |    |
cgtcaatcatgatggttcaatctcaacaacaagatttaagaacaataatataagttttgatcaaccatatgcggcattat  7760
gcagttagtactaccaagttagagttgttgttctaaattcttgttattatattcaaaactagttggtatacgccgtaata
  |                                                                   |     |    |
 7687                                                                7738  7746 7751
            EcoRII
  PfIMI     AvaII                     SspI    AvaI                  FokI
    |         ||                        |       |                     |
acccatctgttggaccagggatatactacaaaggcaaaataatatttctcgggtatggaggtcttgaacatccaataaat  7840
tgggtagacaacctggtccctatatgatgtttccgttttattataaagagcccatacctccagaacttgtaggttattta
    |         ||                        |       |                     |
  7763      7772                      7801    7808                  7829
            7775
```

*Fig. 10*

```
           SmaI
BsmI       BsrI    AvaI              BsmAI        SfaNI        StyI
 |          |      |                   |            |           |
gagaatgcaatctgcaacacaactgggtgtcccgggaaaacgcagagaagctgcaatcaggcatctcatagtccttggtt  7920
ctcttacgttagacgttgtgttgacccacagggccttttgcgtctctctgacgttagtccgtagagtatcaggaaccaa
 |          |      |                   |            |           |
7843       7862   7871                7887         7901        7913
                  7871

HindII
         FokI       HindII                           Eco57I      EcoRV
          |  |        |                                |           |
ttcagacagaaggatggtcaactccattattgttgttgacaagggctcaaactcaattccaaagctgaaggtatggacga  8000
aagtctgtcttcctaccagttgaggtaataacaacaactgttcccgaatttgagttaaggtttcgacttccatacctgct
          |  |        |                                |           |
         7932        7955                             7985        7999
         7937

BsmAI     BsrI                                    BglII        BglII
 |         |                                       |            |
tatccatgagacaaaattactgggggtcagaaggaaggctacttctactaggtaacaagatctatatatatacaagatct  8080
ataggtactctgtttaatgaccccagtcttccttccgatgaagatgatccattgttctagatatatatatgttctaga
 |         |                                       |            |
8008      8019                                    8058         8075 acaagttggcatagcaagttacaattaggaataattgatattactgattacagtgatataagaataaaatggacatggca  8160
tgttcaaccgtatcgttcaatgttaatccttattaactataatgactaatgtcactatattcttatttttacctgtaccgt StyI
                         NcoI
           EcoRII        DsaI              FokI
             |            |                 |
taatgtgctatcaagaccaggaaacaatgaatgtccatggggacattcatgcccagatggatgtataacaagagtatata  8240
attacacgatagttctggtccttttgttacttacaggtaccccctgtaagtacgggtctacctatatattgtcctcatatat
             |            |                 |
           8177          8195              8219
                         8195
                         8195

SfaNI
BsaBI                                       PlaI                      BsrI
 |                                           |                         |
ctgatgcatatccactcaatcccacagggagcattgtgtcatctgtcatattagactcgcaaaaatcgagagtaaaccca  8320
gactacgtataggtgagttagggtgtccctcgtaacacagtagacagtataatctgagcgttttagctctcatttgggt
 |                                           |                         |
8243                                        8294                      8318
8243
```

```
                                                            SspI
                                                            VspI
                                           MboII            AseI
                                             |              | |
cactagacagaaaataaaactcaataaattagataaaagacaacgatctattagaagattaaaattaatattaactgaga  8880
gtgatctgtcttttattttgagttatttaatctatttctgttgctagataatcttctaattttaattataattgactct
                                             |              | |  .
                                           8854            8864
                                                            8864
                                                              8867

EcoRII
                                                    EcoRV              SexAI
                                                     |                  | |
aagtgaatgacttaggaaaatacacatttattagatatccagaaatgtcaaaagaaatgttcaaattacatatacctggt  8960
ttcacttactgaactcttttatgtgtaaataatctataggtctttacagttttctttacaagtttaatgtatatggacca
                                                     |                  | |  .
                                                   8914                8954
                                                                         8955

Tsp45I                                                         BglII
              |                                                             |
attaacagtaaagtgactgaattattacttaaagcagatagaacatatagtcaaatgactgatggattaagagatctatg  9040
taattgtcatttcactgacttaataatgaatttcgtctatcttgtatatcagtttactgactacctaattctctagatac
              |                                                             |
            8973                                                          9032

VspI
 VspI                                                         AseI
 AseI                                             MboII       |
  |                                                 |         |
gattaatgtgctatcgaaattagcctcaaaaaatgatggaagcaattatgatcttaatgaagaaattaataatatatcaa  9120
ctaattacacgatagctttaatcggagttttttactaccttcgttaatactagaattacttctttaattattatatagtt
  |                                              |.        |
9042                                            9099
9042                                                       9105
                                                            9105

XcmI                                MboII
                                       |                                    |
aagttcacacaacctataaatcagataaatggtataatccattcaaaacatggttcactatcaagtatgatatgagaaga  9200
ttcaagtgtgttggatatttagtctatttaccatattaggtaagttttgtaccaagtgatagttcatactatactctcct
                                       |.                                   |  .
                                     9159                                 9196
                                                         MboII    XmnI
   BcgI          Tsp45I                                  EbsI    MboII
    |              |                                      |      |
ttgcaaaaagctcgaaatgaggtcacttttattatggggaaagattataacttgttagaagaccagaagaatttcttatt  9280
aacgttttttcgagctttactccagtgaaaattataccccctttctaatattgaacaatcttctggtcttcttaaagaataa
    |              |                                      |.    |  .
  9203           9222                                   9258   9266
                                                         9258   9266
```

*Fig. 1r*

```
         FokI           SspI
          |              |
   gatacatccagaattggttttaatattagataaacaaaactataatggttatctaattactcctgaattagtattgccgt  9360
   ctatgtaggtcttaaccaaaattataatctatttgttttgatattaccaatagattaatgaggacttaatcataacggca
          |              |
         9285          9302
         Tsp45I                       NspI
          |                            |
   attgtgacgtagttgaaggccgatggaatataagtgcatgtgctaagttagatccaaaattacaatctatgtatcagaaa  9440
   taacactgcatcaacttccggctaccttatattcacgtacacgattcaatctaggttttaatgttagatacatagtcttt
          |                            |
         9364                         9396
                                                                           EcoRV
                                                                            |
   ggcaataatctgtgggaagtgatagataaattgtttccaattatgggagaaaagacatttgatgtgatatcattattaga  9520
   ccgttattagacacccttcactatctatttaacaaaggttaatacccctcttttctgtaaactacactatagtaataatct
                                                                            |
                                                                           9506
                    BspHI                              DraI
                     |                                  |
   accacttgcattatctctaattcaaactcatgatcctgttaaacaattaaggggagcttttttaaatcatgtgttatccg  9600
   tggtgaacgtaatagagattaagtttgagtactaggacaatttgttaattcccctcgaaaaaatttagtacacaataggc
                     |                                  |
                    9548                               9581
                   XbaI  ClaI
                    |     |
   agatggaattgatatttgaatctagagaatcgattaaagaatttctgagtgtagattacattgataaaatcttagatata  9680
   tctaccttaactataaacttagatctcttagctaatttcttaaagactcacatctaatgtaactatttttagaatctatat
                    |     |
                  9621   9629
                                                           FokI
                                                           SfaNI
                                                           | |
   tttaataaatctacaatagatgaaatagcagagattttctcttttttagaacatttgggcatcctccattagaggctag  9760
   aaattatttagatgttatctactttatcgtctctaaaagagaaaaaaatcttgtaaacccgtaggaggtaatctccgatc
                                                           | |
                                                          9740
                                                          9741
                                                           VspI
        BbvI                                               AseI
         |                                                  |
   tattgcagcagaaaaagttagaaaatatatgtatattgggaaacaattaaaatttgacactattaataaatgtcatgcta  9840
   ataacgtcgtcttttcaatcttttatatacatataacccttgttaattttaaactgtgataattatttacagtacgat
         |                                                  |
        9765                                              9822
        Bsp1407I                                          9822
```

*Fig. 1s*

```
        Bsp14071
MboII                                                    Tsp451    BcII
  |       |                                                 |         |
tcttctgtacaataataattaacggatatagagaaaggcatggtggacagtggcctcctgtgacattacctgatcatgca    9920
agaagacatgttattattaattgcctatatctctttccgtaccacctgtcaccggaggacactgtaatggactagtacgt
  |       |            .           .            .           |         .|         .
9841                                                       9900      9911
     9846

NdaI
     EcoRI                              EcoRV
       |                                  |  |
cacgaattcatcataaatgcttacggttcaaattctgcgatatcatatgaaaacgctgttgattattaccagagctttat    10000
gtgcttaagtagtatttacgaatgccaagtttaagacgctatagtatacttttgcgacaactaataatggtctcgaaata
  |                  .|.         .            |   .            .           .
9924                 9959
                        9964
                                    MboII
                                      |                                    BsmAI
                                                                             |
aggaataaaatttaataaattcatagaacctcagttagatgaagatttgacaatttatatgaaagataaagcattgtctc    10080
tccttatttaaattatttaagtatcttggagtcaatctacttctaaactgttaaatatactttctatttcgtaacagag
  .           .            .            |           .            .         |
                                       10041                              10076
                                              FokI
      BsrI               SfaNI                SfaNI                MboII
        |                  |                   ||                    |
caaaaaaatcaaactgggacacagtttctcctgcatctaatttactgtaccgtactaacgcatccaacgaatcacgaaga    10160
gttttttagtttgaccctgtgtcaaagaggacgtagattaaatgacatggcatgattgcgtaggttgcttagtgcttct
  .      |          .      |            .            ||          .          |
        10093            10113                      10140                  10156
                                                    10141
                 BsaBI                                        BsrI
                   |                                            |
ttagttgaaaaatttatagcagatagtaaatttgatcctaatcagatattagattatgtagaatctggggactggttaga    10240
aatcaacttttttaaatatcgtctatcatttaaactaggattagtctataatctaatacatcttagaccccctgaccaatct
  .            .           |            .            .            .         |.
                          10194                                            10231
                                                   PleI
         SspI                                      AccI
           |                                         ||
tgatccagaatttaatatttcttatagtcttaaagaaaaagagatcaaacaagaaggtagactctttgcaaaaatgacat    10320
actaggtcttaaattataaagaatatcagaatttcttttttctctagtttgttcttccatctgagaaacgttttactgta
  .           |            .            .            .            ||          .
             10254                                               10297
                                                                10300
                    BsmAI                                                 FokI
                      |                                                     |
ataaaatgagagctacacaagttttatcagagacactacttgcaaataatataagggaaattctttcaagaaaatgggatg   10400
tattttactctcgatgtgttcaaaatagtctctgtgatgaacgtttattatatcccttaagaaagttcttttaccctac
  .           .            |            .            .            .         |.
                          10350         Fig. 1t                            10396
```

```
                                            AflII                                                            OsaI            BstII07I
                                                                                                                             AccI
gtaaaaggagagattgaattacttaagagattaacaaccatatcaatatcaggagttccacggtataatgaagtatacaa    10480
cattttcctctctaacttaatgaattctctaattgttggtatagttatagtcctcaaggtgccatattacttcatatgtt
                  |                                                                  |              |
                10422                                                              10458          10473
                                                                                                  10473
            MsIII                                                        MboII
gaattctaaaagtcatacagatgatcttaaaacctacaataaaataagtaatctcaatttgtcttctaatcagaaatcaa   10560
attaagattttcagtatgtctactagaattttggatgttattttattcattagagttaaacagaagattagtctttagtt
      |                                                            |
    10494                                                         10542
  EcoRI   HindII                              BsmAI                              BglII
agaaatttgaattcaagtcaacggatatttacaatgatggatacgagactgtgagctgttttctaacaacagatctcaaa   10640
tctttaaacttaagttcagttgcctataaatgttactacctatgctctgacactcgacaaaagattgttgtctagagttt
|     |                                        |                                   |
10569 10577                                  10605                               10631
                                                              SspI
              BsaBI                                          BstXI
aaatactgtcttaattggagatatgaatcaacagctctatttggagaaacttgcaaccaaatatttggattcaataaatt   10720
tttatgacagaattaacctctatacttagttgtcgagataaacctctttgaacgttggtttataaacctaatttatttaa
              |                                              |
            10660                                           10697
                                                            10700
                                  HphI
gtttaattggttacaccctcgtcttgaaggaagtacaatctatgtaggtgatccctattgtcctccatcagataaggaac   10800
caaattaaccaatgtgggagcagaacttccttcatgttagatacatccactagggataacaggaggtagtctattccttg
                                  |
                                10767
  HphI
atatatcattagaggatcaccctgattctggatttatgttcataacccaagaggggtatagaaggattttatcaaaaa   10880
tatatagtaatctcctagtgggactaagacctaaaatacaagtattgggttctcccccatatcttcctaaaacagttttt
  |
10817
                          PvuII
                          NspBII
                          BbvI                                              BsrDI
ttgtggacactcatatctataagtgcaatacatctagcagctgttagaataggcgtaagggtaactgcaatggttcaagg   10960
aacacctgtgagtatagatattcacgttatgtagatcgtcgacaatcttatccgcattcccattgacgttaccaagttcc
                          ||                                                |
                        10917                                              10947
                        10918
         *Fig. 1u*      10918
```

```
                          HphI                 FokI      BspHI
                           |                    |         |
agataatcaagctatagctgtaacaacaagagtacccaacaattatgactacagagttaagaaggagatagtttataaag 11040
tctattagttcgatatcgacattgttgttctcatgggttgttaatactgatgtctcaattcttcctctatcaaatatttc atgtggtgagatttttttgattcattaagagaagtaatggatgatctaggtcatgaacttaaattaaatgaaacaattata 11120
tacaccactctaaaaaaactaagtaattctcttcattacctactagatccagtacttgaatttaatttactttgttaatat
  |                           |        |
11045                        11078    11090
                                       MboII
                                     EcoRI                              XbaI
                                       |  |                              |
agtagcaagatgttcatatatagcaaaagaatatattacgatgggagaattcttccccaagctctgaaagcattatctag 11200
tcatcgttctacaagtatatatcgtttcttatataatgctaccctcttaagaaggggttcgagactttcgtaatagatc
                                          |  |                         |
                                        11167                         11196
                                         11171
                                             SfaNI
     MboII     BsmAI          BsaBI  MboII                              MfeI
       |         |              |     |                                   |
atgtgtcttctggtcagagacagtaatagacgaaacaagatcagcatcttcaaacttggcaacatcatttgcaaaagcaa 11280
tacacagaagaccagtctctgtcattatctgctttgttctagtcgtagaagtttgaaccgttgtagtaaacgttttcgtt
    |           |              |    |                                      |
  11206       11217           11239 11247                                 11278
                                11244
                     SphI
                     NspI
        EcoNI        CacBI                                       FokI
        HphI          |                                     StyI BsaBI
         | |          |                                      |    ||
ttgagaatggttattcacctgttctaggatatgcatgctcaattttttaagaacattcaacaactatatatattgcccttggg 11360
aactcttaccaataagtggacaagatcctatacgtacgagttaaaaattcttgtaagttgttgatatataacgggaaccc
         | |          |                                      |    ||
       11295        11313                                   11354 11360
         11298      11313                                         11359
                    11313
                                                     SfaNI
                                                     FokI        SfaNI
                                                      ||           |
atgaatatcaatccaactataacacagaataacaaagatttatattttaggaatccaaattggatgcaatatgcatctttt 11440
tacttatagttaggttgatattgtgtcttatagtttctaaatataaaatcctaggtttaacctacgttatacgtagaaa
                                                     ||          |
                                                   11422        11433
                                                     11423
                 BalI
  BspMI          MsII                 SspI
    |             ||                    |
aatacctgctagtgttgggggattcaattacatggccatgtcaagatgttttgtaaggaatattggcgatccatcagttg 11520
ttatggacgatcacaaccccctaagttaatgtaccggtacagttctacaaaacattcctataaccgctaggtagtcaac
    |             ||                    |
  11444         11471                  11499
       Fig. 1v   11472
```

```
AciI                                                                                              SexAI
 |                                                                                                  |
ccgcattagctgatattaaaagatttattaaggcgaacctattagaccgaagtgttctttataggattatgaatcaagaa    11600
ggcgtaatcgactataattttctaaataattccgcttggataatctggcttcacaagaaatatcctaatacttagttctt
|       .       .       .       .       .       .       .       .       .       |
11521                                                                                             11600
        PleI
        HphI
EcoRII                     BsrI  Eco57I   MsII
 | | |                      |     |        |
ccaggtgagtcatctttttggactgggcttcagacccatattcatgcaatttaccacaatctcaaaatataaccactat    11680
ggtccactcagtagaaaaaacctgacccgaagtctgggtagaagtacgttaaatggtgttagagttttatattggtgata
| | |   .       .  |    |*      |       .       .       .       .       .       .
11601           11623 11629   11638
   11604
      11607
                                HphI
                                 |
gataaaaaatataacagcaagaaatgtattacaagattcaccgaatccattattatctggattattcacaaatacaatga   11760
ctattttttatattgtcgttctttacataatgttctaagtggcttaggtaataatagacctaataagtgtttatgttact
        .       .       .       .  |    .       .       .       .       .
                                 11718

MboII
  MboII      MboII                                                            XbaI
   |          |                                                                |
tagaagaagatgaagaattagctgagttcttgatggacaggaaggtaattctccctagagttgcacatgatattctagat   11840
atcttcttctacttcttaatcgactcaagaactacctgtccttccattaagaaggatctcaacgtgtactataagatcta
   |       |  .    .       .       .       .       .       .       .       |
   11763  11772                                                              11834
        11766
                                                                              BseRI
                                                                                |
aattctctcacaggaatcagaaatgctatagctggaatgttagatacgacaaaatctctaattcgggttggcataaatag   11920
ttaagagagtgtccttagtctttacgatatcgaccttacaatctatgctgttttagagattaagcccaaccgtatttatc
        .       .       .       .       .       .       .       .       .       |
                                                                                11920 aggaggactgacatacagtttgttgaggaaaatcagtaattacgatctagtacaatatgaaacactaagtaggactttgc   12000
tcctcctgactgtatgtcaaacaactcctttagtcattaatgctagatcatgttatactttgtgattcatcctgaaacg
                                                                        HgaI
         MboII          AccI          BsrDI
          |              |             | |
gactaattgtaagcgacaaaatcaggtatgaagatatgtgttcggtagaccttgctatagcattgcgtcaaaagatgtgg   12080
ctgattaacattcgctatttagtccatacttctatacacaagccatctggaacgatatcgtaacgcagttttctacacc
        .       |       |        .    |  .       .       .       .       .
              12030    12045         12061
                                         12065
```

Fig. 1w

```
                 FokI                                                            HphI
                  |                                                               |
attcatttatcaggaggaaggatgataagtggacttgaaacacctgatccattagaattactatctggggtgataataac  12160
taagtaaatagtcctccttcctactattcacctgaactttgtggactaggtaatcttaatgatagaccccactattattg
     |                                                                        |
   12100                                                                    12149
                   Eco57I
                   MboII                 BstXI        FokI            SspI
                    ||                     |            |              |
aggatcggaacattgtaaaatatgttattcttcagatggcacaaacccatatacttggatgtatttaccgggtaatatta  12240
tcctagccttgtaacatttatacaataagaagtctaccgtgtttgggtatatgaacctacataaatggcccattataat
                    ||                   |            |              |
                  12189                12207        12217           12234
                   12190
                                                      Tsp45I
                                                      AlwNI       BglII
                                                       ||           |
aaataggatcagcagaaacaggtatatcatcattgagagttccttatttggatcagtcactgatgagagatctgaggca  12320
tttatcctagtcgtctttgtccatatagtagtaactctcaaggaataaaacctagtcagtgactactctctagactccgt
                                                       ||           |
                                                     12295        12309
                                                       12297
MfeI              BspMI     AciI         BsrDI
 |                  |         |            |
caattgggatatatcaagaatcttagtaaacctgcaaaagccgcaataagaatagcaatgatatatacatgggcatttgg  12400
gttaaccctatatagttcttagaatcatttggacgttttcggcgttattcttatcgttactatatatgtacccgtaaacc
 |                  |         |            |
12321              12350    12361        12375
                                     PmlI
                                     BsaAI
        EcoRV  FokI  StuI            AfIII                       BsmAI
          |     |     |               ||                           |
taatgatgagatatcttggatggaggcctcacaaatagcacaaacacgtgcaaatttttacactagatagtctcaaaattc  12480
attactactctatagaacctacctccggagtgtttatcgtgtttgtgcacgtttaaaatgtgatctatcagagttttaag
          |     |     |               ||                           |
        12410 12418 12424            12444                       12469
                                      12445
                                      12445
                                                                  BsrI
     AgeI                                                         GsuI
      |                                                            ||
taacaccggtagctacatcaacaaatttatcacacagattaaaggatagtgcaacccagatgaagttctccagtacatca  12560
attgtggccatcgatgtagttgtttaaatagtgtgtctaatttcctatgacgttgggtctacttcaagaggtcatgtagt
      |                                                            ||
    12485                                                        12548
                                                                   12550
```

Fig. 1x

```
                                              Eso311
                                              BsmAI
                        NspI                  BsaI        BsaBI
            MsII        AflIII                |           |
            |           |
ttgattagggtcagcagattcataacaatgtccaatgataacatgtctatcaaggaagctaatgagaccaaagataccaa  12640
aactaatcccagtcgtctaagtattgttacaggttactattgtacagatagttccttcgattactctggtttctatggtt
         •|          •           •|                    |      |        •
          12581                   12601                 12624  12633
                                  12601                 12624
                                                        12624

HpaI        SspI
                        HindII      BstBI                     MboII
                        |           | |                       |
tcttatttatcaacaaataatgttaacaggattaagtgttttcgaatatttatttagattagaagaaaccacaggacaca  12720
agaataaatagttgtttattacaattgtcctaattcacaaaagcttataaataaatctaatcttctttggtgtcctgtgt
         •|         •   |         •|  |        •           •|               •
          12662          12681                  12702
          12662          12685

BsgI                                                 VspI      AccI
         MsII    SfaNI    MboII                                       AseI      PleI
         |       | |      |                                           |         | |
accccatagttatgcatctgcacatagaagatgagtgttgcattaaagaaagttttaatgatgagcatattaatccagag  12800
tggggtatcaatacgtagacgtgtatcttctactcacaacataatttctttcaaaattactactcgtataattaggtctc
 |      •   |  | •       |      •              •              •          | •       | |
  12725     12734         12747                                           12789     12798
                 12738                                                    12789     12800
         VspI    KpnI                               BsrBI
         AseI    BanI                               AciI
         |       |                                  |
tctacattagaattaattaggtaccctgaaagtaatgaatttatttatgataaagacccgctcaaggacgtggacttatc  12880
agatgtaatcttaattaatccatgggactttcattacttaaataaatactatttctgggcgagttcctgcacctgaatag
         •|       |       •            •           •            |•
          12812   12820                                          12858
          12812   12820                                          12858
                              MfeI          FokI              NspI
                              |             |                 |
aaaacttatggttattaaagatcattcttacacaattgatatgaattattgggatgatactgacatcatacatgcaattt  12960
ttttgaataccaataatttctagtaagaatgtgttaactatacttaataacccactatgactgtagtatgtacgttaaa
         •         •          |         •   |         •      |         •
                              12913          12932            12950
                 AhdI   Tsp45I                                  BsrDI
                 |      |                                       |
caatatgtactgcaattacaatagcagacactatgtcacaattagatcgagataacttaaaagagataatagtcattgca  13040
gttatacatgacgttaatgttatcgtctgtgatacagtgttaatctagctctattgaattttctctattatcagtaacgt
         •      |      |        •             •            •       •            •
                12987   12995                                                    13034
```

Fig. 1y

```
                VspI
                AseI                          PleI              AfIII
                 |                             |                  |
  aatgatgatgatatattaatagcttaatcactgaattttgactcttgatatacttgtatttcttaagacatttggtggatt  13120
  ttactactactataattatcgaattagtgacttaaaaactgagaactatatgaacataaagaattctgtaaaccacctaa
       .      |      .      .      .     |•      .      .     •|      .      .
           13053                       13079                13101
           13053
                                            DraI    AvaII
                                             |     PpuMI
                                             |      ||
  attagtaaatcaatttgcatacactctttatagtttaaaaaccgaaggtagggacctcatttgggattatataatgagaa  13200
  taatcatttagttaaacgtatgtgagaaatatcaaattttggcttccatccctggagtaaaccctaatatattactctt
       .      .      .      |      .      .    •||      .      .      .      .
                         13154                13171
                                              13172
                SspI                                  FokI
                 |                                     |
  cactgagagatacttcccattcaatattaaaagtattatctaatgcattatctcatcctaaagtattcaagaggttctgg  13280
  gtgactctctatgaagggtaagttataattttcataatagattacgtaatagagtaggatttcataagttctccaagacc
       .      |      .      .      .      .      |      .      .      .      .
           13223                                13254
    PleI                                                                      SspI
     |                                                                         |
  gattgtggagtcttaaaccctatttatggccctaatactgctagtcaagaccagataaaacttgccctctctatatgtga  13360
  ctaacacctcagaatttgggataaataccgggattatgacgatcagttctggtctattttgaacgggagagatatacact
  |•      .      .      .      .      .      .      .      .      .      .      |
  13288                                                                      13360
         BglII                                                Tsp45I
           |                                                     |
  atattcactagatctatttatgagagaatggttgaatggtgtatcacttgaaatatacatttgtgacagcgatatggaag  13340
  tataagtgatctagataaatactctcttaccaacttaccacatagtgaactttatatgtaaacactgtcgctataccttc
       |      .      .      .      .      .      .      |      .      .      .
    13370                                             13423
                      XbaI                                         SfaNI    AvaII
                       |                                             |       |
  ttgcgaatgataggaaacaagcctttatttctagacacctttcatttgtttgttgtttagcagaaattgcatcttttgga  13520
  aacgcttactatcctttgttcggaaataaagatctgtggaaagtaaacaaacaacaaatcgtctttaacgtagaaaacct
       .      .      |      .      .      .      .      .      .     |•      |•
                  13470                                           13509   13518
                  BsmAI                                      SspI
                   |                                          |
  cctaacctgttaaacttaacatacttagagagacttgatctattgaaacaatatcttgaattaaatattaaagacgaccc  13600
  ggattggacaatttgaattgtatgaatctctctgagctagataactttgttatagaacttaatttataatttctgctggg
       .      |      .      .      .      .     |      .      .      .      .
           13550                              13584
```

*Fig. 1z*

```
                              PacI
                              VspI                               SnaBI
          Bsp14071            AseI                               BsaAI
             |                 ||                                 |
   cattcttaaatatgtacaaatatctggattattaattaaatcgttcccatcaactgtaacatacgtaagaaagactgcaa   13680
   gtaagaatttatacatgttatagacctaataattaatttagcaagggtagttgacattgtatgcattctttctgacgtt
        |              •||        •         •         •      |        •         •
      13613           13631                                 13662
                      13631                                 13662
                      13632
                                                    BamHI
           SspI              Bsu36I         BsaBI         MboII
            |                  |              |  |          |
   tcaaatatttaaggattcgtggtattagtccacctgaggtaattgatgattgggatccgatagaagatgaaaatatgctg   13760
   agtttataaattcctaagcaccataatcaggtggactccattaactactaaccctaggctatcttctacttttatacgac
      |          •         •     |       •    |  |     •        |         •        •
    13684                      13713        13728       13743
                                              13733                        HaeII
                                                                           Eco47III
                                                                             |
   gataacattgtcaaaactataaatgataattgtaataaagataataaaggggaataaaattaacaatttctggggactagc   13840
   ctattgtaacagttttgatatttactattaacattatttctattatttcccttatttttaattgttaaagacccctgatcg
      •         •         •         •         •         •         •         •    |
                                                                                13838
                  AvaII                                                         13838
          AfIII   PpuMI        BglII                               SfaNI        AgeI
            |      ||            |                                   |           |
   gcttaagaactatcaggtccttaaaatcagatctataacaagtgattctgataataatgatagatcagatgctagtaccg   13920
   cgaattcttgatagtccaggaatttagtctagatattgttcactaagactattattactatctagtctacgatcatggc
      |      •||           |•        •         •        •         •         |•    |•
    13842  13855         13869                                           13908  13917
           13856
                                       MfeI                    SpeI
                                        |                       |
   gtggtttgacacttcctcaaggggggaattatctatcacatcaattgagattattcggaatcaacagcactagttgtctg   14000
   caccaaactgtgaaggagttccccccttaatagatagtgtagttaactctaataagccttagttgtcgtgatcaacagac
      •         •         •         |         •     •   |         •         •
                                    13962                     13989
                                                        StyI
                                                        MboII
                                                        Ksp632I
                                                        EarI
                                             EcoRII     SapI    AvrII
                                               |         |||     |
   aaagctcttgagttatcacaaattttaatgaaggaagttaataaagaccaggacaggctcttcctaggagaaggagcagg   14080
   tttcgagaactcaatagtgtttaaaattacttccttcaattatttctggtcctgtccgagaaggatcctcttcctcgtcc
      •         •         •         •         •        |•        |||•  |
                                                     14048      14057 14063
                                                                14058
                                                                14058
                      Fig. 1aa                                  14059
                                                                     14063
```

```
                                    PstI
              NspI                  BspMI
         NheI                       AvaII
         Cac8I         SfaNI        PpuMI
           |  |          |          ||| |
     agctatgctagcatgttatgatgccacattaggacctgcagttaattattataattccggtttgaatataacagatgtaa  14160
     tcgatacgatcgtacaatactacggtgtaatcctggacgtcaattaataatattaaggccaaacttatattgtctacatt
     |  •|          |          •|| | |                                         •
     14087         14100         14111
     14087                        14112
        14091                      14114
                                    14116

SspI
         HindII     XmnI      Eco57I                                   Tsp45I
            |        | |        |                                        |
     ttggtcaacgagaattgaaaatattcccttcagaggtatcattagtaggtaaaaaattaggaaatgtgacacagatcctt  14240
     aaccagttgctcttaactttttataaggggaagtctccatagtaatcatccattttttaatcctttacactgtgtctaggaa
       |        |        |                                                  |
     14164      14177    14188                                              14226
                    14180
                                                                       BsmBI
         ScaI                   XcmI                             BsmI  BsmAI
           |                     |                                |     |
     aatagggtaaaagtactgttcaatggaaatccaaattcaacatggataggaaatatggaatgcgagacgttaatatggag  14320
     ttatcccattttcatgacaagttaccctttaggtttaagttgtacctatcctttataccttacgctctgcaattataactc
          |                     |                                |  •|
         14252                 14271                            14298 141304
                                                                     141304
                                                                      XmnI
                                                                      MboII
                                                                      |  |
     tgaattgaatgataagtctattggattggtacattgtgatatggaaggagctatcggtaaatcagaagaaactgttctac  14400
     acttaacttactattcagataacctaaccatgtaacactataccttcctcgatagccatttagtcttcttcgacaagatg
                                                                       |  |
                                                                     14385
                                                                       14388

MsII                       FokI
           |                         |
     atgaacactatagtgttataagaattacatacttgattggggatgatgatgttgttttaatttccaaaattatacctaca  14480
     tacttgtgatatcacaatattcttaatgtatgaactaaccccctactactacaacaaaattaaaggttttaatatggatgt
           |                         •|
         14406                      14441
             XbaI
              |
     atcactccgaattggtctagaatactttatctatataagttatattggaaagattgaagtataatatcacttaaaacttc  14560
     tagtgaggcttaaccagatcttatgaaatagatatattcaatataaccttctacattcatattatagtgaattttgaag
                 |
              14496
                                                          Fig. 16b
```

```
       SfaNI                         SfaNI
        |                              |
taatcctgcatcaacagaattatatctaatttcaaaagatgcgtattgtactataatggaacctagtgaagttgttttat  14640
attaggacgtagttgtcttaatatagattaaagttttctacgcataacatgatattaccttggatcacttcaacaaaata
|·         ·        ·        |·        ·        ·        ·        ·        ·
14568                       14598

Tsp45I   MboII                                      MboII
                   |       |                                           |
caaaacttaaaagattgtcactcttggaagaaaataatctattaaaatggatcatttatcaaagaagaaaaataatgaa   14720
gttttgaattttctaacagtgagaaccttcttttattagataattttacctagtaaaatagtttcttcttttattactt
|·        ·       | |·         ·        ·        ·        ·       | ·        ·
                14657 14667                                      14705

Eco31I
                                              BsmAI
          BspHI                                BsaI       NdeI
            |                                   |          |
tggttacatcatgaaatcaaagaaggggaaagagattatggagttatgagaccatatcatatggcattacaaattttttgg 14800
accaatgtagtactttagtttcttccccttttctctaatacctcaatactctggtatagtataccgtaatgtttaaaaacc
|·        ·        ·        ·        ·        ·       | ·       |·        ·
14729                                                14768      14778
                                                     14768
                                                     14768

OraI                              BglII
    SwaI                         GsuI   |
    ||                            |     |
atttcaaatcaatttaaatcatctggcgaaagaattttatcaactccagatctgactaatatcaacaatataatccaaa   14880
taaagtttagttaaatttagtagaccgctttcttaaaaatagttgaggtctagactgattatagttgttatattaggttt
|·|       ·        ·        ·        ·| ·       |·        ·        ·        ·
14812                                14845
14813                                14849
                     VspI
          FokI      AseI       BspHI         BsmAI          AciI
           |         |           |             |             |
gttttcagagaacaatcaaggatgttttgtttgaatggattaatataactcatgatggtaagaagcataaattaggcggg  14960
caaaagtctcttgttagttcctacaaaacaaacttacctaattatattgagtactaccattctctgtatttaatccgccc
|·        ·       |·        |·           |       ·   |    ·      |·
         14900            14919         14930      14942         14956
                          14919
                                                               SpeI
                                                              MboII
                                                              BbsI
                                                              |  |
agatataacatattcccactgaaaaataaggggaaattaagactgctatcgagaagactagtattaagttggatttcatt  15040
tctatattgtataagggtgacttttattccccttttaattctgacgatagctcttctgatcataattcaacctaaagtaa
|·        ·        ·        ·        ·        ·       | |·        ·        ·
                                                     15013
                                                     15013
      Fig. 1cc                                                 15017
```

```
                                        SduI
       PleI                             HgiAI   BsrI
        |                                 |      |
       gtcattatcgactcgattacttacaggtcgtttttcctgatgaaaaatttgaacatagagcacagactggatatgtgtcat 15120
       cagtaatagctgagctaatgaatgtccagcaaaaggactacttttaaacttgtatctcgtgtctgacctatacacagta
         |                                         |    |
       15050                                     15097 15105
                                                  15097
       tacctgatactgatttagaatcattaaagttattgtcgaaaaacaccattaagaattacagagagttgatagggtcaata 15200
       atggactatgactaaatcttagtaatttcaataacagcttttttgtggtaattcttaatgtctctcacatatcccagttat EcoRI
                                                              |
       tcatattggttttaaccaaagaagttaaaatacttatgaaattgattggtggtgctaaattattaggaattcccagaca 15280
       agtataaccaaagattggtttcttcaattttatgaatactttaactaaccaccacgatttaataatccttaagggtctgt
                                                                |
                                                              15268

MboII
          MboII   BbsI
           |       |
       atataaggaacccgaagaacagttattagaagactacaatcaacatgatgaatttgatatagattaaaatacaaatacaa 15360
       tatattccttgggcttcttgtcaataatcttctgatgttagttgtactacttaaactatatctaattttatgtgtatgtt
             |          |
           15294       15309
                       15309
                                                          NspI
                                                          AflIII
                                                  L end     |----->Trailer
       taaagatatatcctaacctttatcattaagcctaaagatagacaaaagtaagaaaaacatgtaatatatatatataccaaa 15440
       atttctatataggattggaaatagtaattcggatttctatctgttttcattcttttt gtacattatatatatatggttt
                                                                |
                                                              15418
                                                              15418
         MboII
          |
       cagagttcttctcttgtttggt 15462
       gtctcaagaagagaacaaacca
         |
       15447
```

*Fig. 1dd*

INFECTIOUS CLONE FOR HUMAN PARAINFLUENZA VIRUS TYPE 3

This application claims the benefit of U.S. Provisional Application No. 60/045,805, which has a filing date of May 7, 1997.

This work was supported in part by National Institutes of Health Grant No. 32027 from the Institute of Allergy and Infectious Diseases. The government may have rights in this invention.

BACKGROUND

Recognized in 1956 as a cause of respiratory infection in man, human parainfluenza viruses (HPIV) are believed to account for 4 to 22 percent of the respiratory illnesses in children, second only to respiratory syncytial virus in this regard. HPIV are important causes of the lower respiratory tract diseases such as pneumonia and bronchiolitis, and are the most common cause of croup in young children. Of the four HPIV serotypes, 1–4, type 3 virus (HPIV-3), appears to be the most virulent, frequently causing bronchiolitis and pneumonia during the first month of life.

Unfortunately, effective vaccines or antiviral therapies, which can be used to prevent or treat HPIV-induced infections, are not presently available. Standard methods which are used to produce inactive MAH viruses, such as heat inactivation or chemical treatment of the virus, have been unsuccessful with all HPIV strains and serotypes, including HPIV-3. Moreover, standard methods for producing attenuated viruses produce mutations at random sites and do not allow one to modify the HPIV genome at specific sites or to control the number of mutations that are introduced into genome.

Human parainfluenza viruses are enveloped, single-stranded, negative sense RNA viruses that are members of the paramyxovirus genus within the family Paramyxoviridae. Replication of the human parainfluenza viral genome (vRNA) is similar to that of other members of the Paramyxoviradae family. Upon infection of a cell, transcription is the major RNA synthetic event, resulting in the production of the viral mRNAs from the negative-sense genome, i.e., the vRNA. Later in infection a transition to RNA replication occurs, resulting in synthesis of a full-length, antigenomic, positive-sense RNA, which serves as the template for synthesis of additional negative-sense genomic RNA. Transcription and replication of the genomic RNA is dependent upon formation of a ribonucleoprotein complex (RNP) consisting of the 15462 nucleotide genomic RNA encapsidated by the nucleocapsid protein (NP), and the closely associated phosphoprotein (P), and the large (L) polymerase protein. Several host cell factors are also involved in the replicative cycle of HPIV.

The requirement for an intact RNP for HPIV has hindered analysis of HPIV transcription and replication in a cell-free system. Efforts to encapsidate HPIV-3 vRNA in vitro have failed, and unlike the positive sense RNA viruses, naked HPIV vRNA is not infectious. Moreover, there currently are no known systems for preparing recombinant HPIV, including recombinant infectious HPIV-3.

Accordingly, there is a need for new reagents, systems, and methods that enable one to produce a recombinant HPIV, particularly a recombinant, infectious HPIV-3. Recombinant systems that permit one to introduce one or more site-specific mutations into the genome of HPIV, particularly HPIV-3, are desirable. Recombinant systems which allow one to characterize the effect of site-specific mutations on the transcription or replication of human parainfluenza viral RNA and to identify the site specific mutations which lead to the production of attenuated HPIV are especially desirable.

SUMMARY OF THE INVENTION

In accordance with the present invention a system for generating recombinant, human parainfluenza virus, particularly infectious, recombinant, human parainfluenza virus type 3 (HPIV-3) is provided. In one embodiment, the system comprises a clone comprising a nucleotide sequence that encodes a full-length, positive sense, anti-genome of HPIV, and at least one support clone comprising a nucleotide sequence that encodes the HPIV P protein and the HPIV L protein. In another embodiment, the system further comprises a support clone which comprises a nucleotide sequence that encodes the HPIV NP protein. Preferably, each of the clones in the system comprises an RNA polymerase promoter which is operatively linked to the respective HPIV nucleotide sequence contained within the clone.

The present invention also provides a clone which comprises a nucleotide sequence encoding the full-length, positive sense, anti-genome of HPIV-3. The clone also comprises an RNA polymerase promoter operatively linked to the HPIV-3 antigenome-encoding sequence. In a preferred embodiment, the clone further comprises a nucleotide sequence which encodes a ribozyme immediately downstream from the sequence encoding the HPIV-3 antigenome.

The present invention also relates to a method of preparing recombinant HPIV-3 virus having site-specific mutations in the HPIV-3 genome. The method comprises preparing a clone comprising a modified HPIV-3 antigenome-encoding sequence; introducing the modified HPIV-3 clone and support clones which comprise nucleotide sequences encoding an HPIV-3 P protein, an HPIV-3 L protein, and, preferably, an HPIV-3 NP protein into host cells.; and culturing the host cells under conditions that allow for synthesis of the modified HPIV-3 antigenome and the L, P, and NP proteins of HPIV-3.

The ability to produce recombinant, HPIV-3 virus genetically engineered to contain site-specific mutations within the HPIV-3 genes and cis-acting elements expedites the study of all aspects of the virus replication cycle. Additionally, a system which permits production of recombinant HPIV that is genetically engineered to contain site-specific mutations within the HPIV-3 genome is useful for identifying attenuating parainfluenza genotypes and for developing a live vaccine for human parainfluenza virus.

BRIEF DESCRIPTION OF THE FIGURES

FIG. 1 depicts the DNA form of the nucleotide sequence of the HPIV-3 genome and shows the location of restriction sites, the leader sequence, the trailer sequence, and the protein encoding regions of the genome.

DETAILED DESCRIPTION OF THE INVENTION

Figure 2:
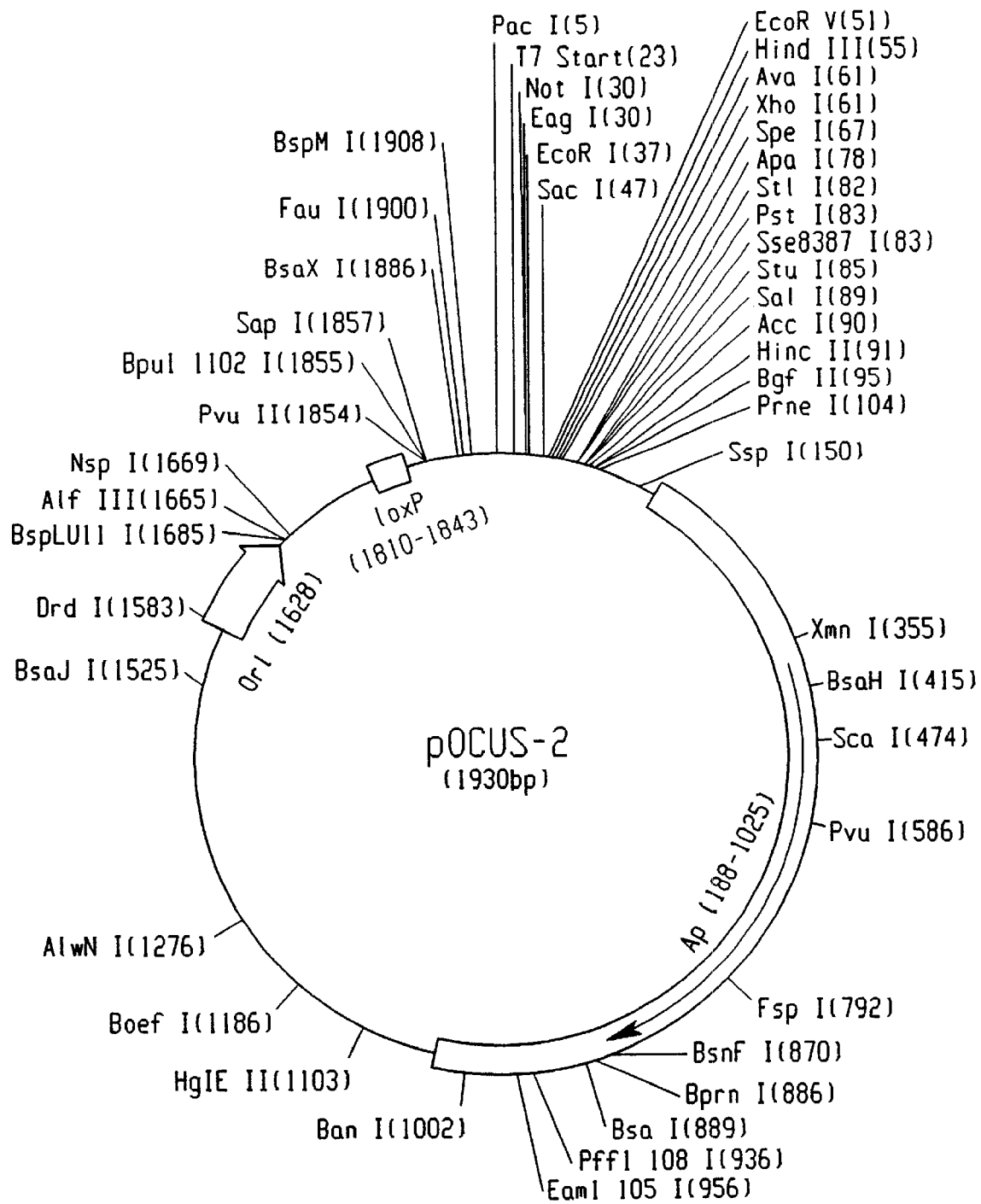
FIG. 2 is a restriction map of the pOCUS-2™ vector.

In accordance with the present invention a system for generating recombinant, human parainfluenza virus is provided. In a preferred embodiment, the system is used to generate recombinant HPIV-3. The system comprises a clone comprising a nucleotide sequence, preferably a double-stranded DNA sequence, which encodes a full-length, positive sense anti-genome of HPIV hereinafter referred to as the "HPIV clone", and one or more support clones which comprise nucleotide sequences that encode an HPIV P protein and an HPIV L protein. The nucleotide sequences that encode the HPIV P protein and HPIV L protein may be within the same clone. However, for ease of manipulation, it is preferred that the nucleotide sequences that encode the HPIV P protein and the HPIV L protein be on separate clones. Preferably the HPIV clone comprises a sequence encoding an HPIV-3 antigenome. Preferably the support clone or clones encode a P protein and an L protein of HPIV-3. In another embodiment the system further comprises a support clone which comprises a nucleotide sequence that encodes the HPIV NP protein, preferably the HPIV-3 NP protein.

As used herein "clone" refers to double-stranded DNA that can be introduced into a cell and expressed. The clone may be in the form of a viral vector such as, for example, a vaccinia viral vector, or, preferably, in the form of a plasmid. Preferably, the HPIV clone and the support clones each comprise an RNA polymerase promoter, more preferably a T7 RNA polymerase promoter. Each of the RNA polymerase promoters is operatively linked to the corresponding HPIV encoding sequence in the clone. Thus, the RNA polymerase promoter on the HPIV clone is operatively linked to the HPIV sequence and the RNA polymerase on the support clones are operatively linked to the sequence or sequences encoding the respective HPIV protein. Preferably, the plasmids comprising the clone also comprise an origin of replication, particularly a bacterial origin of replication.

Figure 1Q:
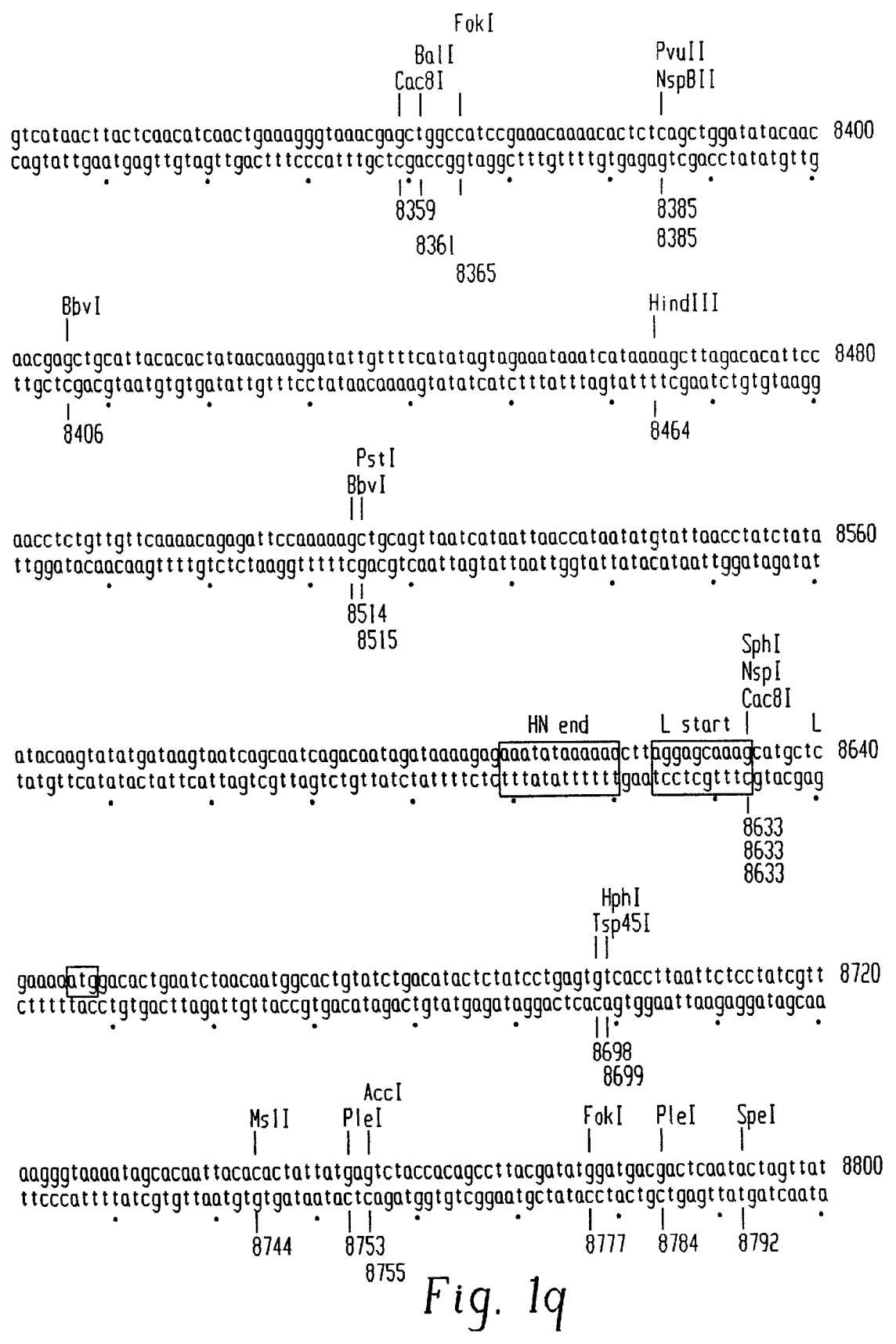

The present invention also provides a clone which comprises a nucleotide sequence encoding the anti-genomic sequence of HPIV-3, hereinafter referred to as the "HPIV-3 clone". Preferably, the HPIV-3 clone encodes a full-length antigenomic sequence of HPIV-3. As used herein "full-length" means that the anti-genomic sequence is complementary to the entire negative sense, genomic sequence of HPIV-3 extending from the 3' MAH nucleotide of the leader sequence through the 5' MAH nucleotide of the trailer sequence of the HPIV-3 genome. The DNA form of the full-length, genomic sequence of HPIV-3, SEQ ID NO:1, is shown in FIG. 1. In addition to the leader and trailer sequences, the HPIV-3 clone contains sequences encoding the HPIV-3 proteins N, P, M, F, HN, and L, as well as the cis-acting elements. The HPIV-3 clone may encode a wild-type HPIV-3 antigenome sequence or a modified HPIV-3 antigenome having one or more mutations contained therein. The mutation may be in the form of a foreign gene which is inserted into the HPIV-3 antigenome-encoding sequence. Preferably, the mutations are substitutions of one or more nucleotides, deletions of 3 to 12 nucleotides, or additions of 3 to 12 nucleotides in the HPIV-3 antigenome-encoding sequence. More preferably, the modified HPIV-3 clone contains substitutions either in the genes or the cis-acting elements, or both of the HPIV-3 antigenome-encoding sequence.

Figure 5:
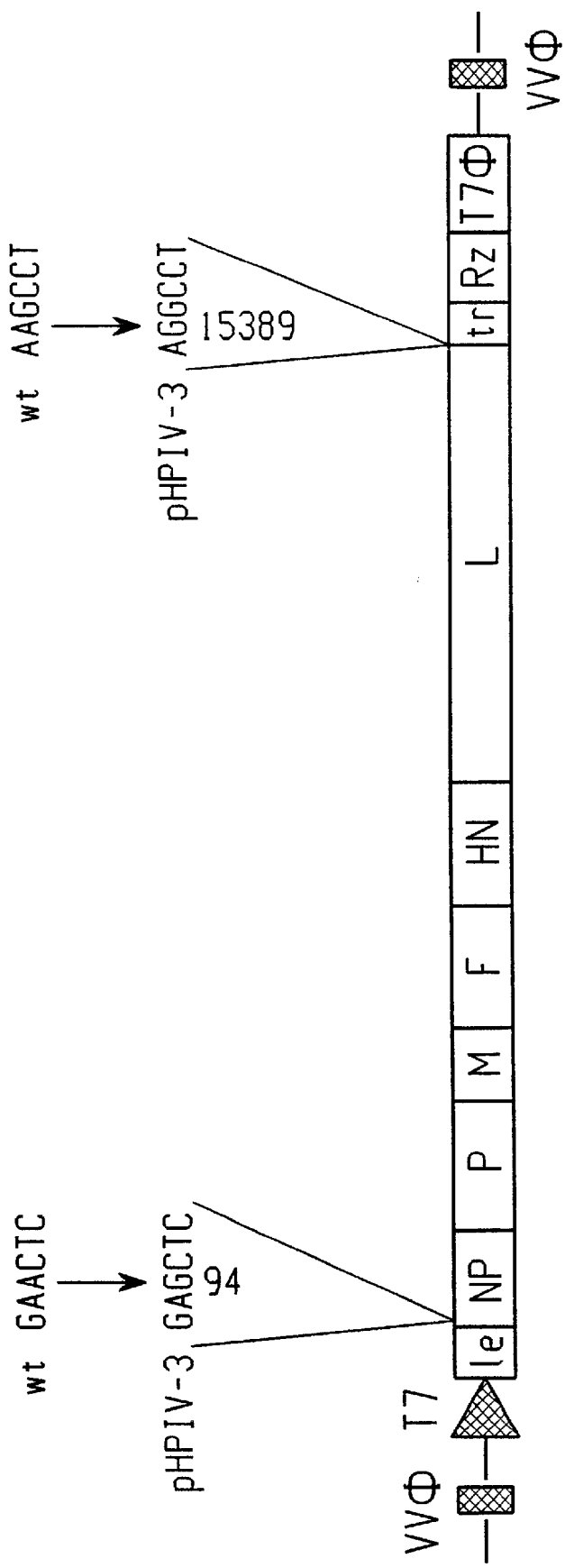
FIG. 5 is a schematic depiction of the full-length infectious clone, pHPIV-3. VVφ, vaccinia virus polymerase stop signal (TTTTTNT); T7, T7 RNA polymerase promoter; le, HPIV-3 leader sequence; NP, P, M, F, HN and L are the HPIV-3 protein coding regions; tr, HPIV-3 trailer sequence; Rz, the hepatitis delta virus antigenomic ribozyme; T7φ, T7 RNA polymerase terminator signal. Regions containing substitution mutations are expanded and shown above with the specific changes indicated. The A to G change at viral base 94 creates a SacI site and the A to G change at viral base 15389 creates a StuI site.

Preferably, the HPIV-3 clone is a plasmid that comprises a nucleotide sequence which encodes a ribozyme, more preferably the hepatitis delta virus antigenomic ribozyme, immediately downstream from the HPIV antigenome-encoding sequence. Following transcription of the clone, the ribozyme cleaves the ribozyme from the HPIV antigenome to provide a replication competent 3' end on the antigenome. More preferably, the HPIV-3 clone also comprises an RNA polymerase terminator following the ribozyme sequence. In one embodiment, the HPIV-3 clone is the plasmid pHPIV-3 depicted in FIG. 5, which plasmid was deposited with the American Type Culture Collection, 10801 University Boulevard, Manassas, Va. 20110-2209, USA, on Sep. 17, 1999, and has Accession Number PTA-722.

The present invention also relates to a method of preparing recombinant HPIV, particularly HPIV-3, using the above described system. The method comprises introducing an HPIV clone and the support clones which encode HPIV P protein and HPIV L protein, into host cells, preferably human cells; culturing the host cells under conditions that allow for formation of an HPIV anti-genomic transcript, synthesis of the HPIV genome (vRNA) and the HPIV proteins L, P, and NP, and formation of a recombinant HPIV; and recovering the recombinant HPIV from the culture. Preferably the host cells which are transfected with the HPIV clone and support clones, contain an RNA polymerase that corresponds to the RNA polymerase promoter that is operatively linked to the HPIV sequences in the HPIV clone and the support clones. In a preferred embodiment, a support clone comprising the nucleotide sequence which encodes the HPIV-NP protein operatively linked to an RNA polymerase promoter is also introduced into the cells. Preferably, the host cells are infected with a viral recombinant, preferably a vaccinia virus recombinant, which expresses the RNA polymerase, more preferably the T7 RNA polymerase, prior to or in combination with transfection with the HPIV clone and support clone or clones. When such cells are infected with the vaccinia virus recombinant, it is preferred that the HPIV-3 clone also comprise a vaccinia virus RNA polymerase terminator upstream of the T7 RNA polymerase and a vaccinia virus RNA polymerase terminator downstream of the T7 RNA polymerase terminator.

The present invention also relates to a method of introducing site-specific mutations into the genome of a recombinant HPIV-3. The method comprises preparing a a modified HPIV-3 clone comprising one or more mutations in the sequence which encodes the HPIV-3 anti-genome; introducing the modified HPIV-3 clone and support clones comprising sequences which encode HPIV-3 P protein and HPIV-3 L protein, and preferably, HPIV-3 NP protein into host cells; and culturing the host cells under conditions that allow for formation of a modified HPIV-3 antigenomic transcript and synthesis of the HPIV-3 L, P, and NP proteins. The modified HPIV-3 clone and the support clones contain an RNA polymerase promoter that is operatively linked to the HPIV-3 protein-encoding sequences. The host cells contain within the cytoplasm thereof an RNA polymerase that corresponds to the RNA polymerase promoter on the modified HPIV-3 clone and the support clones.

Preferably, the modified HPIV-3 clone, containing one or more mutations therein, is made by conventional PCR techniques using an HPIV-3 clone as a template. The mutations are made in the cis-acting elements of the HPIV-3 sequence or in an HPIV-3 protein encoding sequence. Preferably the mutation is made in the L protein-encoding sequence. If mutations are made in the HPIV-3 protein-encoding sequences of the HPIV-3 clone, it is preferred that a similar type of mutation be made in the same site in the protein encoding sequence of the corresponding support clone. For example, if a mutation is made at a specific site in the L protein-encoding sequence of the HPIV-3 clone, it is preferred that the same mutation be made at the same site in the L protein-encoding sequence of the L protein-encoding support clone. Such method is useful for identifying mutations that block the synthesis of viral particles or result in the production of non-infectious or non-virulent HPIV-3.

To determine whether the mutated viruses produced by the above-described method are non-virulent, i.e., attenuated, the mutated viruses are first tested in vitro to determine whether the mutation has resulted in a slower growing phenotype, i.e., the mutated virus grows more slowly in tissue culture than the wild-type virus. The mutated viruses which exhibit this phenotype are then examined in vivo, by injection into an animal, such as the cotton rat, which is good experimental model for parainfluenza virus. The infected animals are then examined to determine if they are producing antibodies to HPIV-3 and to determine if there is a reduction in the severity of symptoms as compared to animals infected with wild-type virus.

The ability to produce recombinant HPIV-3 virus genetically engineered to contain specific alterations within the HPIV-3 genes and cis-acting elements expedites the study of all aspects of the virus replication cycle. Additionally, a system which permits production of recombinant HPIV that is genetically engineered to contain specific alterations within the HPIV-3 genes is useful for identifying attenuating parainfluenza genotypes and for developing a live vaccine for human parainfluenza virus.

The following examples of methods of preparing a full-length cDNA clone of HPIV-3 and methods of preparing a modified or mutated, infectious, recombinant HPIV-3 are for purposes of illustration and are not intended to limit the scope of the invention.

EXAMPLE 1
Construction of a Full-Length cDNA Clone of HPIV-3

The construction of a full-length infectious clone of HPIV-3 containing mutations at specific sites was achieved by a two-step process. The initial step was the generation of a minireplicon which contained the positive sense leader portion region and trailer regions of HPIV-3. The second step involved the insertion of RT-PCR fragments derived from HPIV-3 genomic RNA into the minireplicon. The positive-sense minireplicon contained the following: A T7 promoter which directed the synthesis of two non-viral G residues, followed by the positive-sense leader region of HPIV-3, a portion of the NP 5' UTR (to viral base 97), the luciferase gene, a portion of the L 3'UTR (starting at viral base 15387) and trailer sequences of HPIV-3. The full-length nucleotide sequence of HPIV-3 genome and the location of the leader sequence, trailer sequence and protein-encoding regions is shown in FIG. 1. The hepatitis delta virus antigenomic ribozyme followed to effect precise cleavage after the 3 terminal HPIV-3 specific base. A T7 RNA polymerase terminator was also incorporated into the replicon followed the ribozyme sequence. Additionally, vaccinia virus polymerase termination signals were inserted immediately upstream and downstream of the aforementioned sequences. During the construction, single base changes were created in the regions encoding the NP 5' UTR and the L 3 UTR. An A to G change at viral base 94 and the A to G change at base 15389 created SacI and StuI sites, respectively, which served as genetic tags to identify virus as being of recombinant origin.

The vector pOCUS-2 (Novagen) was chosen as the starting plasmid for preparing the mini-replicon [pPIV3-MG(+)], because of its small size (1930 bp). It is believed that the use of a small starting plasmid may increase the stability of the full-length clone.

The mini-replicon was constructed by generating PCR products encoding the leader and trailer regions flanked by a T7 promoter and hepatitis delta virus antigenomic ribozyme, respectively. The primers used for synthesis of the T7 promoter/leader region were: 5'-TAGTCGGCCC TAATACGACTCACTATAGGACCAAACAAGAGA AGAA ACT-3', SEQ ID NO:2, and 5'-GAAATTATAGAGCTCCCTTTTCT-3', SEQ ID NO:3. The first primer encodes an EagI site and the T7 promoter (underlined) and the second primer introduced an A to G base change at viral base 94, (bold) within the 5' untranslated region (UTR) of the NP mRNA, which creates a SacI site. The template for this reaction pHPIV3-CAT, described in De, B. P. and A. K. Banerjee. (1993.) Rescue of synthetic analogs of genome RNA of human parainfluenza virus type 3. Vir. 196:344–348, which is incorporated herein by reference. The resulting PCR product was cloned into the EagI and SacI sites of pOCUS-2, which is depicted in FIG. 2. The primers used for synthesis of the trailer/ribozyme region were:
5'-TAAGGCCTAAAGATAGACAAAAAGTAAGAAA AACATGTAATATATATA TACCAAACAGAGTTCT- TCTCTTGTTTGGTGGG TCGGCATGGCATCTC-3', SEQ ID NO:4, and 5'-CTGGGTAC CTCCCTTAGCCATCCGAGT-3', SEQ ID NO:5. The first primer contains sequence from the 3' UTR of the L mRNA, through the trailer, and primes synthesis of the ribozyme (underlined). Also, an A to G change at viral base 15389 (bold), which creates a StuI site within the 3'UTR of the L mRNA is encoded by this primer. The second primer encodes the 3' end of the ribozyme (underlined) and a BglII site. The template for this PCR reaction was pSA1, a plasmid containing the ribozyme sequence, as previously described in Perrotta, A. T. and M. D. Been. 1991. The pseudoknot-like structure required for efficient self-cleavage of hepatitis delta virus RNA. Nature 350:434–436, which is incorporated herein by reference. The PCR product derived from this reaction was cloned into the StuI and BglII sites of pOCUS-2. The leader and trailer regions were combined into a single clone by transferring the EagI/PstI fragment of the T7/leader clone into the PacI/PstI sites of the trailer/ribozyme clone.

Figure 3:
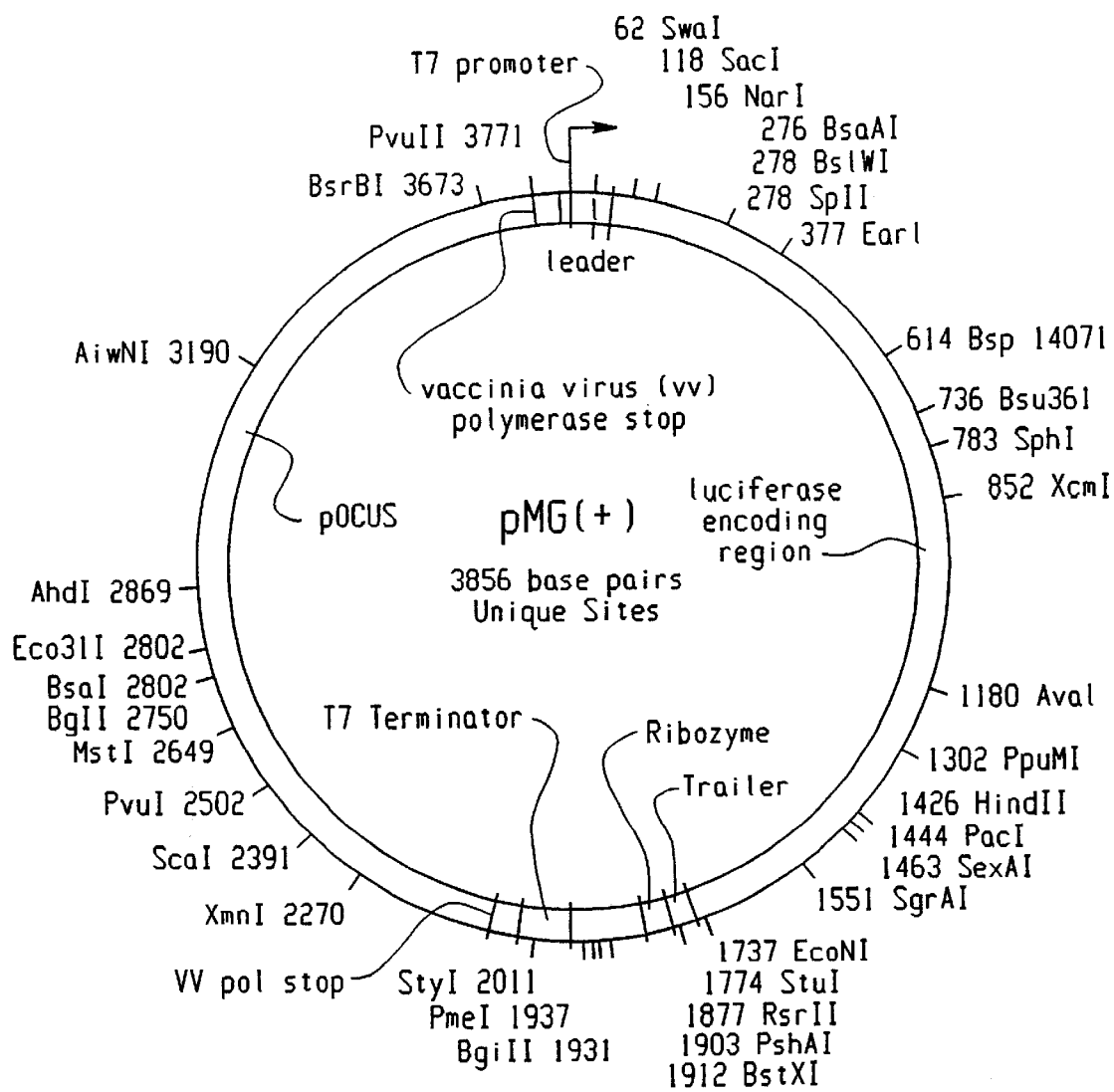
FIG. 3 is a restriction map of pMG(+) showing the location of the leader sequence, luciferase encoding region, and the T7 promoter and terminator.
Figure 4:
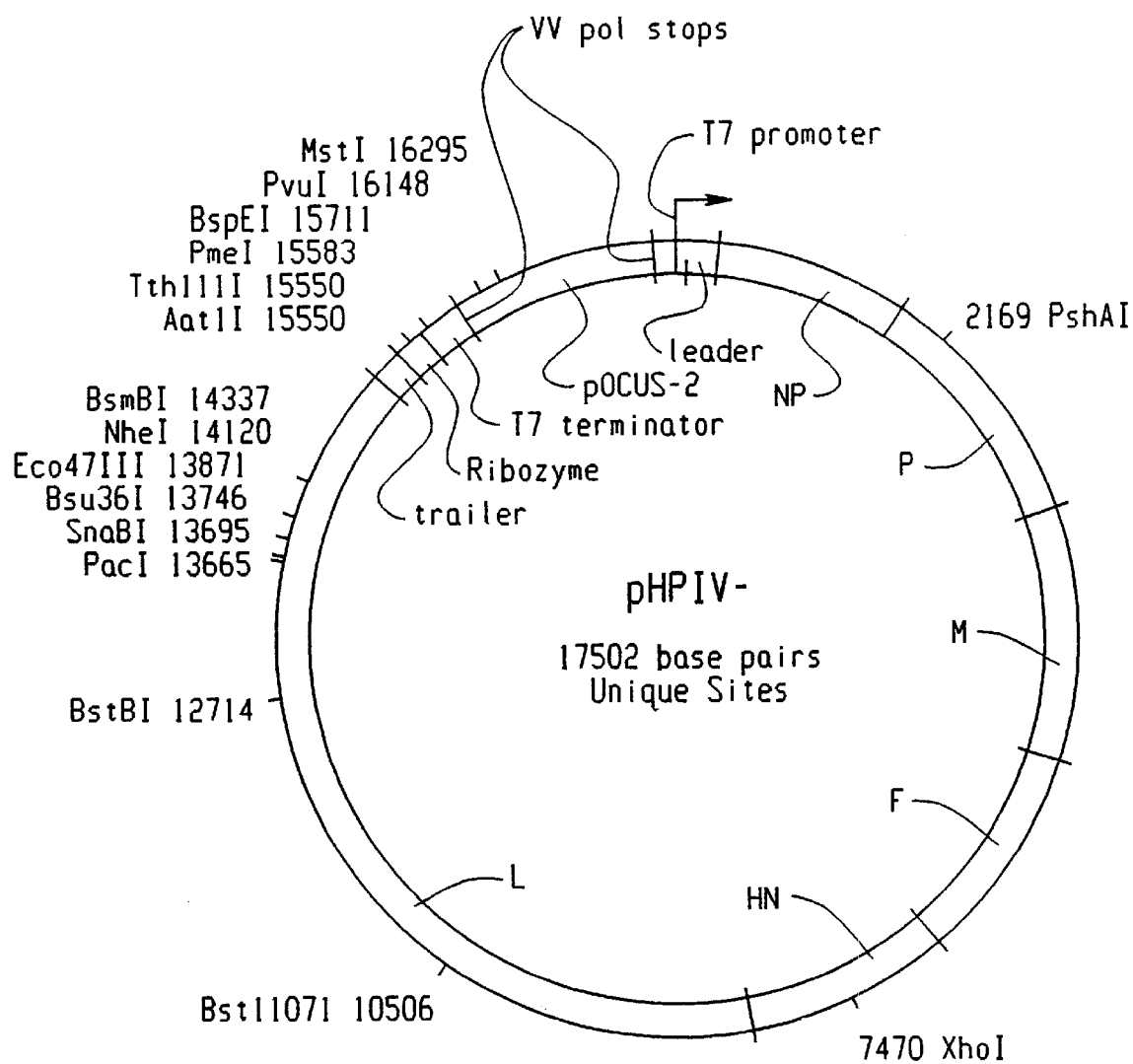
FIG. 4 is a restriction map of pHPIV-3 showing the location of the leader sequence and the protein encoding regions of HPIV-3.

To prevent possible interference by transcription from cryptic vaccinia virus promoters, vaccinia virus polymerase transcription stop signals (TTTTTNT) were inserted upstream and downstream of the replicon near PvuII and SspI sites within pOCUS-2. A T7 transcription termination signal was removed from pET-17b by digesting with BlpI and BspEI, and inserted into the SspI site (blunted with T4 DNA polymerase) of pOCUS-2. A luciferase reporter gene was then inserted into the SacI and StuI sites to create pPIV3-MG(+), which is schematically depicted in FIG. 3.

To generate the full-length HPIV-3 clone, five RT-PCR products were generated from HPIV-3 virion RNA and cloned. These fragments were subsequently inserted into pPIV3-MG(+), replacing the luciferase coding sequences, to create pHPIV-3, the full-length clone. The five RT-PCR products were generated from HPIV-3 strain 47885 virion RNA which was obtained from Robert Chanock, at the National Institutes of Health. These PCR products, encompassing the remainder of the HPIV-3 genome, were identified by restriction enzyme analysis and cloned, either in pUC19 or pOCUS-2, and then inserted into pPIV3-MG(+).

The first PCR product containing viral bases 83 to 2721 was inserted into the SmaI site of pUC19. The 83/2721 clone was then digested with SacI and XmnI, removing viral bases 94 to 553 which were inserted into the SacI and SphI (blunt with T4 DNA polymerase) of pPIV3-MG(+). The 83/2721 clone was then digested with PstI to remove a fragment containing viral bases 540 to 2274, which was then inserted into the PstI site of the pPIV3-MG(+) clone containing the 94/554 fragment. The second PCR product encompassing viral bases 13395 to 15397 was cloned into the SmaI site of pUC19. This 13395/15397 clone was then digested with StuI and PacI and the resulting fragment containing viral bases 13632 to 15381 was inserted into the StuI and PacI sites of the pPIV3-MG(+) clone containing viral sequence to base 2274. The resulting clone contained viral bases 1 to 2274 and 13632 to 15462 in the pPIV3-MG(+) context.

The third PCR product containing viral bases 7403 to 11513 was digested with BspMI (blunted with T4 DNA polymerase) and XhoI to produce a fragment containing bases 7437 to 11444 which was inserted into the XhoI and SspI sites of pOCUS-2. The fourth PCR fragment containing viral bases 10904 to 13773 was digested with PvuII and BamHI (viral bases 10918 to 13733) and inserted into the EcoRI (blunted with T4 DNA polymerase) and BamHI sites of pUC19. The two viral segments were combined by digesting the 7437/11444 clone with SacI (blunted with T4 DNA polymerase) and EcoNI and inserting into the 10918/13733 clone digested with EcoRI (blunted with T4 DNA polymerase) and EcoNI. The resulting clone contained viral bases 7437 to 13733 in a pUC19 background. The remainder of the viral sequence was derived from a fifth PCR product encompassing viral bases 83 to 7457 which had been digested with XmnI and XhoI (viral bases 553 to 7437) and cloned into the StuI and XhoI sites of pOCUS-2. The 7437/13733 clone was then digested with BamHI, blunted with T4 DNA polymerase, and digested with XhoI to release a fragment that was inserted into the EagI (blunted with T4 DNA polymerase) and XhoI digested 553/7437 clone. The resulting clone contained viral bases 553 to 13733. This clone was then digested with PshAI and PacI and the resulting fragment containing viral bases 2143 to 13632 was inserted into the same sites of the pPIV3-MG(+) clone containing viral bases 1 to 2274 and 13632 to 15462. This generated pHPIV-3, the infectious clone, which is schematically depicted in FIG. 4.

To insert the P gene into pGEM-4, P sequences were transferred from a P-lac-fusion clone, (described in 38, which is incorporated herein by reference) by digesting with XbaI (blunted with T4 DNA polymerase) BamHI, and inserted into the KpnI (blunted with T4 DNA polymerase) and BamHI sites of pGEM4. The pPIV3-NP and pPIV3-L clones, as described in 15, 16, which are incorporated herein by reference., were in a pGEM-4 background. The pPIV3-L clone was also modified. In the natural L mRNA sequence there is a non-initiating AUG 11 nucleotides from the 5' end of the transcript. This was removed from pPIV3-L by mutational PCR, changing viral bases 8636 and 8637 from AT to TA.

EXAMPLE 2

Preparation of Recombinant HPIV-3

Confluent monolayers of HeLa cells in 6-well plates were infected with recombinant vaccinia virus vTF7-3 at a multiplicity of infection of 2. vTF7-3 expresses T7 RNA polymerase as described in. Fuerst, T. R., P. L. Earl, and B. Moss. 1987. "Use of a hybrid vaccinia virus-T7 RNA polymerase system for expression of target genes." Mol. Cell. Biol. 7:2538–2544, and Fuerst, T. R., E. G. Niles, F. W. Studier, and B. Moss. 1986. "Eukaryotic transient-expression system based on recombinant vaccinia virus that synthesizes bacteriophage T7 RNA polymerase." Proc. Natl. Acad. Sci. 83:8122–8126, which are incorporated herein by reference. After 1 hour at 37° C., pPIV3-NP, pPIV3-P, pPIV3-L and pHPIV-3 were transfected using Lipofectin (BRL) according to manufacturers instructions. After three hours the transfection medium was removed and replaced with 1.5 ml Dulbecco's modified Eagle's medium (DMEM)/5% fetal bovine serum. After 40 to 48 hours the plates were frozen, thawed and scraped. The clarified medium supernatant (250 $\mu$l) was then used to infect fresh HeLa cell monolayers in 6-well plates. DMEM (1.5 ml) containing 25 $\mu$g/ml 1-B-D-arabinofuranosylcytosine (araC) to inhibit vaccinia virus replication was added after a 1 hour attachment. After forty hours the plates were frozen, thawed, and scraped. The clarified medium supernatant was then titered for HPIV-3 in the presence of AraC. During the titering, isolated plaques were picked as agar plugs. The agar plugs were placed in 500 ml opti-MEM at 4° C. for 4 hr. 250 $\mu$l were then used to infect fresh HeLa cell monolayers for amplification of the plaque isolates for 40 hr.

In a preferred embodiment transfection conditions were 1 $\mu$g pHPIV-3, 2 $\mu$g pPIV3-NP, 4 $\mu$g pPIV3-P and 0.1 $\mu$g pPIV3-L. Under these conditions approximately 1000 pfu per $6\times10^5$ cells were obtained during the initial transfection and $10^6$ pfu per $6\times10^5$ cells after the amplification.

When individual plasmids were omitted from the transfection step it was observed that the pHPIV-3, pPIV3-P and pPIV3-L plasmids were required for recovery of virus but, surprisingly, as shown in Table 1 below, pPIV3-NP was not.

TABLE 1

| Plasmids Transfected HPIV-3 | NP | P | L | Virus Recovery |
|---|---|---|---|---|
| + | + | + | + | 14/15[a] |
| − | + | + | + | 0/2 |
| + | − | + | + | 3/3[b] |
| + | + | − | + | 0/3 |
| + | + | + | − | 0/2 |

Table 1. Recovery of HPIV-3 from pHPIV-3. HeLa cell monolayers were infected with vTF7-3 and transfected with the indicated plasmids. After 40 hr cells were lysed and supernatants added to fresh HeLa cell monolayers in the presence of araC to inhibit vTF7-3 replication. These monolayers were then lysed and the supernatants assayed for HPIV-3. The number of experiments for which HPIV-3 was recovered per attempts is displayed under virus recovery.

Characterization of Recovered Virus

In order to characterize the recovered virus and to purify HPIV-3 from vTF7-3, plaques of which are only slightly smaller than those of HPIV-3, isolated plaques suspected to be HPIV-3 were picked and amplified in HeLa cells. The plaque purified and amplified virus isolates and appropriate controls were then analyzed in neutralization assays. Virus (isolates #3 and #5) was preincubated (30 min on ice) with 5 ul rabbit pre-immune serum, 5 ul rabbit polyclonal anti-HPIV-3 antisera, or assayed in the presence of 25 ug/ml araC The sera was incubated with virus on ice for 30 min prior to a standard plaque assay. To allow maximal plaque development, the plates were then incubated at 37° C. for 66 hr prior to staining with crystal violet. The results of the assay indicated that the plaque purified virus was completely inhibited by the anti-HPIV-3 antisera, while vTF7-3 was not. In contrast, the HPIV-3 isolates were not inhibited by AraC, whereas the vTF7-3 virus was completely inhibited. Interestingly, of the eight recombinant HPIV-3 isolates, four had plaque sizes identical to the parental HPIV-3 stock while four were slightly larger. The plaque size of isolate #3 was slightly larger than isolate #5 and the wild type HPIV-3 virus.

To determine whether the NP coding sequence of pHPIV-3, which shares the same position as luciferase in pPIV3-MG(+), was being expressed from pHPIV-3, pHPIV-3 and pPIV3-NP were separately transfected into vTF7-3 infected HeLa cells and cell lists prepared after 48 hr. The lysates were then analyzed by Western blotting using an anit-HPIV-3RNP antisera. This antisera recognizes primarily NP and reacts poorly with P.

Specifically, extracts (equivalent to $6\times10^4$ cells) were run on SDS-10% PAGE and transferred to nitrocellulose membranes. The primary antibody was a rabbit polyclonal anti-RNP antisera diluted 1:1000. The secondary antibody was 1:1000 dilution of a goat anti-rabbit antibody conjugated to horseradish peroxidase. Visualization was through chemiluminescence (ECL kit, Amersham). As shown by the Western blot, HPIV-3 RNP recognized NP from the pPIV3-NP and pHPIV-3 transfected cell extracts and from purified HPIV-3 RNP. No proteins were recognized in a mock-transfected HeLa extract. Thus, it appears that NP is expressed from pHPIV-3, presumably being translated from the T7-directed, antigenomic RNA transcript.

To determine whether the recovered, recombinant virus had specific mutations in its genome, RNA was extracted from wild type and plaque isolated viruses and used for RT-PCR analysis using primers flanking the substitution mutations. Viral RNA was isolated from approximately $2\times10^7$ plaque forming units (pfu) of plaque purified virus isolates #3, 5, 7 and 9, or wt HPIV-3 strain 47885/. Reverse transcription was carried out using Superscript II reverse transcriptase (BMB) at 44° C. for 1 hr using oligonucleotides which primed at viral base 23 or 15100. The PCR was carried out with Expand Long polymerase (BMB) using second primers which result in amplification of viral bases 23 to 303, or 15100 to 15440.

PCR products encompassing viral bases 1 to 324 and 15080 to 15462 were generated from the indicated isolates, digested with SacI and StuI, respectively, and analyzed on a 1.4% agarose gel. PCR products of the expected sizes were generated in a RT-dependent manner, indicating that the PCR products were derived from RNA rather than contaminating plasmid DNA.

As shown on the agarose gel, the sizes of the 1 to 324 and 15080 to 15462 PCR products are increased by 21 and 22 base pairs, respectively, over the length of the viral specific regions due to the inclusion of restriction enzyme sites in the amplification primers. Digestion with SacI showed that the mutation at base 94 was not present in the wild-type virus but was present in the plaque isolated viruses, indicating they are of recombinant origin. Similarly, PCR product derived from the region encompassing viral base 15389 of wild type HPIV-3 was not cleaved by StuI. However, only four of the eight plaque isolated viruses contained the mutation which creates the StuI site. Direct sequencing of the PCR products confirmed these results.

DISCUSSION

A full-length plasmid clone of the HPIV-3 genome, pHPIV-3 was constructed. Upon transfection of pHPIV-3 and plasmids encoding the viral NP, P and L proteins into vTF7-3-infected HeLa cells, recombinant HPIV-3 bearing genetic markers was efficiently recovered. Several interesting features of this system were noted. First, the viral NP protein could be expressed from the infectious clone, and this expression obviated the need for an NP support plasmid. It is believed that the NP protein is synthesized directly from the primary antigenomic transcript after it is capped by the vaccinia virus capping enzyme.

Second, two recombinant viruses with distinct genotypes and phenotypes were produced, probably due to recombination between the pHPIV-3 and pPIV3-L plasmids, although the possibility that the reversion arises during RNA replication cannot be excluded. pPIV3-L contains the entire L 3' UTR and part of the trailer region, extending to base 15437, an overlap of 48 base pairs beyond the StuI site. This is ample room for recombination between plasmids to occur readily in vaccinia virus infected cells.

From these results, there appears to be selection in the HPIV-3 system. All the large plaque virus isolates had reverted to a wild-type sequence at base 15389, while retaining the change at base 94. Since A94G is the only known alteration in these viruses from the parental virus, it appears that The isolates which retained both mutations had a plaque size identical to that of the parental (wild type) virus, but when the 15389 mutations was lost, plaque size increased, indicating that the mutation at base 15389 was detrimental in the context of the A94G mutation. There was one other known change between pHPIV-3 and the support plasmids. A non-initiating AUG exists in the natural L protein message. Since this AUG is only 11 nucleotides from the 5' end of the L mRNA and in a poor translation initiation context, it may not cause much interference with L mRNA translation. However, in the support plasmid pPIV3-L this non-initiating AUG is much further from the 5' end of the transcript where it is more likely to be recognized by ribosomes. This AUG was removed from pPIV3-L by changing bases 8636 and 8637 from AT to TA, destroying a SphI site and creating a NheI site. To investigate whether this change was present in the recombinant virus and could be responsible for the large plaque phenotype, RT-PCR analysis was done. PCR products encompassing this site and derived from both the wild type and the plaque isolated viruses retained a wild type sequence, indicating recombination had not occurred over this region and that these changes could not account for any variance in plaque size.

The finding that recombination may occur between transfected plasmids indicates that care must be taken when introducing mutations into the paramyxovirus or rhabdovirus infectious clone systems. Mutations introduced within the NP, P or L sequences preferably are carried by both the support plasmids and the infectious clone. Otherwise, resultant virus may not carry the desired mutation. The only possible exception to this is the HPIV-3 system, in which the HPIV-3 infectious clone expresses NP, negating the need for the NP support plasmid. Still, it is preferred that the HPIV-3 NP support plasmid be included in the system, since significantly greater yields of HPIV-3 were obtained when the support NP plasmid was included in the transfection.

An infectious clone for HPIV-3 is useful for understanding the molecular biology of HPIV-3 and for developing a vaccine for this important pathogen. The ability to generate specific mutations within HPIV-3 makes all aspects of HPIV-3 replication amenable to study. Any mutation, including those studied previously in other contexts, can now be examined with this system. The ability to introduce specific mutations also permits the possibility of revertant analysis, which could refine our understanding of protein-protein or protein-RNA interactions.

The infectious clone is also useful for identifying mutations which attenuate the virus. Such virus is useful for developing new vaccine strains of HPIV-3. In addition, mutations present in a current candidate vaccine strain of HPIV-3 can be inserted into pHPIV-3. Through identifying multiple deleterious mutations, it should be possible to engineer several mutations affecting various steps in the virus life cycle into a single HPIV-3 strain. Such a virus should be highly attenuated and not readily able to revert.

While the invention has been described to some degree of particularity, various adaptations and modifications can be made without departing from the scope of the invention as defined in the appended claims.

What is claimed is:

1. A method for preparing recombinant human parainfluenza virus comprising;
   a. providing a recombinant system which comprises:
      i. an HPIV clone comprising a nucleotide sequence encoding a positive sense, antigenome of human parainfluenza virus;
      ii. a support clone comprising a nucleotide sequence encoding a human parainfluenza virus L protein; and
      iii. a support clone comprising a nucleotide sequence encoding a human parainfluenza virus P protein, wherein the nucleotide sequence encoding the P protein and L protein may be on the same support clone or on separate support clones;
   b. introducing the recombinant system of step (a) into host cells;
   c. culturing the host cells of step (b) for a time sufficient to permit transfection of the host cells and formation of recombinant human parainfluenza virus; and
   d. recovering the recombinant human parainfluenza virus from the culture of transfected host cells.

2. The method claim 1 wherein the antigenome-encoding sequence of the HPIV clone is operatively-linked to an RNA polymerase promoter;
   wherein the P protein-encoding sequence of the support clone is operatively-linked to an RNA polymerase promoter;
   wherein the L protein-encoding sequence of the support clone is operatively linked to an RNA polymerase promoter; and
   wherein the host cells comprise an RNA polymerase corresponding to the RNA polymerase promoter of the said HPIV clone and said support clones.

3. The method of claim 2, wherein the host cells are infected with a viral recombinant capable of expressing the RNA polymerase prior to or in combination with introduction of the recombinant system into the host cells.

4. A method of introducing a site-specific mutation into the genome of a recombinant human parainfluenza virus, comprising the following steps:
   a. preparing a clone comprising a nucleotide sequence encoding a human parainfluenza viral antigenome having a mutation at a specifc site;
   b. co-transfecting host cells with the clone of step (a), a support clone comprising a nucleotide sequence encoding an HPIV L protein, and a support clone comprising a nucleotide sequence encoding an HPIV P protein; wherein the nucleotide sequence encoding the P protein and L protein may be on the same support clone or on separate support clones; and
   c. culturing the transfected host cells for a time sufficient to allow formation of a recombinant human parainfluenza virus.

5. The method of claim 4 further comprising the step of transfecting the host cells with a support clone comprising a nucleotide sequence encoding an HPIV NP protein.

6. The method of claim 4 wherein the clone of step (a) is prepared using polymerase chain reaction techniques and a clone comprising a nucleotide sequence encoding a human parainfluenza virus antigenome as a template, wherein the antigenome-encoding nucleotide sequence of said template clone lacks the site specific mutation.

7. A recombinant HPIV clone comprising:
   (a) a nucleotide sequence encoding a positive sense, antigenome of human parainfluenza virus type 3 (HPIV-3); and
   (b) an RNA polymerase promoter operatively linked to said nucleotide sequence.

8. The clone of claim 7 wherein said clone further comprises a ribozyme sequence downstream from said antigenome-encoding sequence.

9. The clone of claim 8 wherein the ribozyme is an antigenomic ribozyme.

10. The clone of claim 8 further comprising an RNA polymerase terminator downstream of the ribozyme sequence.

11. The clone of claim 7 wherein the RNA polymerase promoter is the T7 RNA polymerase promoter.

12. The clone of claim 11 further comprising a vaccinia virus RNA polymerase terminator upstream of the T7 RNA polymerase and a vaccinia virus RNA polymerase terminator downstream of the T7 polymerase terminator.

13. The clone of claim 7 wherein the clone has the American Type Culture Collection Accession Number PTA-722.

14. A recombinant HPIV clone comprising:
   a) a nucleotide sequence encoding a modified, positive sense anti-genome of HPIV-3, and
   b) an RNA polymerase promoter operatively linked to said nucleotide sequence;
   wherein said clone is for preparing an infectious HPIV-3.

15. The clone of claim 14 wherein said antigenome sequence has a mutation in a protein coding region or a mutation in a cis-acting element or a mutation in a protein coding region and a mutation in a cis-acting element, and
   wherein the mutation is selected from the group consisting of a substitution of one or more nucleotides, a deletion of 3 to 12 nucleotides, and an addition of 3 to 12 nucleotides.

16. The clone claim 15 wherein the mutation is in the P protein or the L protein coding sequence.

17. The clone of claim 14 wherein the modified HPIV-3 antigenome sequence has a foreign gene inserted therein.

18. A host cell for producing a recombinant human parainfluenza type 3 virus, said host cell comprising:
   a. an HPIV-3 clone comprising a nucleotide sequence encoding a positive sense, antigenome of human parainfluenza type 3 virus;
   b. a support clone comprising a nucleotide sequence encoding a human parainfluenza virus type 3 L protein; and
   c. a support clone comprising a nucleotide sequence encoding a human parainfluenza virus type 3 P protein;
   wherein the nucleotide sequence encoding the P protein and L protein may be on the same support clone or on separate support clones.

19. The host cell of claim 18 further comprising a support clone comprising a nucleotide sequence encoding a human parainfluenza virus NP protein.

20. A host cell for producing a recombinant human parainfluenza virus type 3, said host cell comprising:
   a. an HPIV clone comprising a nucleotide sequence encoding a positive sense, antigenome of human parainfluenza virus type 3, wherein said antigenome sequence comprises a site-specific mutation;
   b. a support clone comprising a nucleotide sequence encoding a human parainfluenza virus type 3 L protein; and
   c. a support clone comprising a nucleotide sequence encoding a human parainfluenza virus type 3 P protein;
   wherein the nucleotide sequence encoding the P protein and the nucleotide sequence encoding the L protein are on the same support clone or on separate support clones.

21. The host cell of claim 19 wherein the HPIV-3 clone further comprises an RNA polymerase promoter operatively linked to the HPIV-3 antigenomic sequence and wherein each of the support clones comprises an RNA polymerase promoter operatively linked to the HPIV-3 protein-encoding sequence of said support clone.

22. The host cell of claim 20 wherein the site-specific mutation is selected from the group consisting of a substitution of one or more nucleotides, a deletion of 3 to 12 nucleotides, and an addition of 3 to 12 nucleotides.

23. The host cell of claim 20 wherein the HPIV-3 antigenome sequence has a foreign gene inserted therein.

24. A host cell for producing a recombinant human parainfluenza virus, said host cell comprising:
   a. an HPIV clone comprising a nucleotide sequence encoding a positive sense, antigenome of human parainfluenza virus, wherein said antigenome sequence comprises a site specific mutation;
   b. a support clone comprising a nucleotide sequence encoding a human parainfluenza virus L protein; and
   c. a support clone comprising a nucleotide sequence encoding a human parainfluenza virus P protein;
   wherein the nucleotide sequences encoding the P protein and the L protein are on the same support clone or on separate support clones; and
   wherein the mutation is in the L protein coding region of the antigenome encoding sequence of the HPIV clone, and wherein the support clone which comprises the L protein encoding sequence has a corresponding mutation therein.

25. The host cell of claim 24 wherein the HPIV clone comprises a nucleotide sequence encoding a positive sense, antigenome of HPIV-3, and wherein the nucleotide sequence encoding a human parainfluenza virus L protein encodes an HPIV-3 L protein, and wherein the nucleotide sequence encoding the human parainfluenza virus P protein encodes an HPIV-3 P protein.

26. A host cell for producing a recombinant human parainfluenza virus, said host cell comprising:
   a. an HPIV clone comprising a nucleotide sequence encoding a positive sense, antigenome of human parainfluenza virus, wherein said antigenome sequence comprises a site specific mutation;
   b. a support clone comprising a nucleotide sequence encoding a human parainfluenza virus L protein; and
   c. a support clone comprising a nucleotide sequence encoding a human parainfluenza virus P protein;
   wherein the nucleotide sequences encoding the P protein and the L protein are on the same support clone or on separate support clones; and
   wherein the mutation is in the P protein coding region of the antigenome encoding sequence of the HPIV clone, and wherein the support clone which comprises the P protein encoding sequence has a corresponding mutation therein.

27. The host cell of claim 26 wherein the HPIV clone comprises a nucleotide sequence encoding a positive sense, antigenome of HPIV-3, and wherein the nucleotide sequence encoding a human parainfluenza virus L protein encodes an HPIV-3 L protein, and wherein nucleotide sequence encoding a human parainfluenza virus P protein encodes an HPIV-3 P protein.

28. A host cell for producing a recombinant human parainfluenza virus, said host cell comprising:
   a. an HPIV clone comprising a nucleotide sequence encoding a positive sense, antigenome of human parainfluenza virus, wherein said antigenome sequence comprises a site specific mutation;
   b. a support clone comprising a nucleotide sequence encoding a human parainfluenza virus L protein;
   c. a support clone comprising a nucleotide sequence encoding a human parainfluenza virus P protein; and
   d. a support clone comprising a nucleotide sequence encoding a human parainfluenza virus NP protein;
   wherein the nucleotide sequences encoding the P protein, L protein, and NP protein are on the same support clone or on separate support clones and
   wherein the mutation is in the NP protein coding region of the antigenome encoding sequence of the HPIV clone, and wherein the support clone which comprises the NP protein encoding sequence has a corresponding mutation therein.

29. The host cell of claim 28 wherein the HPIV clone comprises a nucleotide sequence encoding a positive sense, antigenome of HPIV-3, and wherein the nucleotide sequence encoding a human parainfluenza virus L protein encodes an HPIV-3 L protein, and wherein nucleotide sequence encoding a human parainfluenza virus P protein encodes an HPIV-3 P protein, and wherein the nucleotide sequence encoding a human parainfluenza virus NP protein encodes an HPIV-3 NP protein.

* * * * *

UNITED STATES PATENT AND TRADEMARK OFFICE
CERTIFICATE OF CORRECTION

PATENT NO. : 6,248,578 B1
DATED : June 19, 2001
INVENTOR(S) : Amiya K. Banerjee, Michael A. Hoffman Page 1 of 1

It is certified that error appears in the above-identified patent and that said Letters Patent is hereby corrected as shown below:

ABSTRACT,
Line 11, after "a" please delete "MAH".

Signed and Sealed this

Fifteenth Day of January, 2002

Attest:

JAMES E. ROGAN
Attesting Officer  Director of the United States Patent and Trademark Office

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 15462 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ACCAAACAAG AGAAGAAACT TGTTCGGAAA TATAAATTTA AATTAAAATT AACTTAGGAT      60

TAAAGACATT GACTAGAAGT CAAGAAAAGG TCAAGAAAAG GGAACTCTAT AATTTCAAAA     120

ATGTTGAGCC TATTTGATAC ATTTAATGCA CGTAGGCAAG AAAACATAAC AAAATCAGCT     180

GGTGGAGCTA TCATTCCTGG ACAGAAAAAT ACTGTCTCCA TATTTGCCCT TGGACCGACA     240

ATAACTGATG ACAATGAGAA AATGACATTA GCTCTTCTAT TTCTATCTCA TTCACTAGAT     300

AATGAGAAAC AACATGCACA AAGGGCAGGG TTCTTGGTGT CTTTATTGTC AATGGCTTAT     360

GCCAATCCAG AGCTTTACCT GACAACAAAT GGAAGTAATG CAGATGTTAA ATATGTCATA     420

TATATGATTG AGAAAGATCT AAAACGGCAA AAGTATGGAG GATTTGTGGT TAAGACGAGA     480

GAGATGATAT ATGAAAAGAC AACTGAGTGG ATATTTGGAA GTGACCTGGA TTATGACCAG     540

GAAACTATGC TGCAGAACGG CAGAAACAAT TCAACGATTG AAGATCTTGT TCACACATTT     600

GGGTATCCAT CATGTTTAGG AGCTCTTATA ATACAGATCT GGATAGTTTT GGTCAAAGCC     660

ATCACTAGCA TCTCAGGGTT AAGAAAAGGC TTTTTCACTC GATTAGAGGC TTTCAGACAA     720

GATGGAACAG TGCAAGCAGG GCTGGTATTG AGCGGTGACA GCGTGGATCA GATTGGGTCA     780

ATCATGCGGT CTCAACAGAG CTTGGTAACT CTTATGGTTG AGACATTAAT AACAATGAAT     840

ACTAGCAGAA ATGACCTCAC AACCATAGAA AAGAATATAC AAATTGTTGG TAACTACATA     900

AGAGATGCAG GTCTTGCTTC ATTCTTCAAT ACAATCAGGT ATGGAATTGA GACTAGAATG     960

GCAGCTTTGA CTCTATCTAC TCTCAGACCA GATATCAATA GATTAAAAGC TCTGATGGAA    1020

TTGTATTTAT CAAAGGGACC ACGCGCTCCT TTTATCTGTA TCCTCAGAGA TCCTATACAT    1080

GGTGAGTTCG CACCAGGCAA CTATCCTGCC ATATGGAGTT ATGCAATGGG GGTGGCAGTT    1140

GTACAAAACA GAGCCATGCA ACAGTATGTG ACGGGAAGAT CATATCTAGA TATTGATATG    1200

TTCCAGCTGG GACAAGCAGT AGCACGTGAT GCTGAAGCTC AGATGAGCTC AACACTGGAA    1260

GATGAACTTG GAGTGACACA CGAAGCCAAA GAAAGCTTGA AAGACATAT AAGGAACATA    1320
```

```
AACAGTTCAG AGACATTTTT CCACAAACCA ACAGGCGGAT CAGCCATAGA GATGGCAATA    1380

GATGAAGAGC CAGAACAATT TGAACACAGA GCAGATCAAG AACAAGATGG AGAACCTCAA    1440

TCATCTATAA TCCAATATGC TTGGGCAGAA GGAAACAGAA GTGATGATCG GACCGAGCAA    1500

GCTACAGAAT CCGACAATAT CAAGACTGAA CAACAAAACA TCAGAGACAG ACTAAACAAG    1560

AGACTCAACG ACAAGAAGAA ACAAGGCAGT CAACCATCCA CCAATCCCAC AAACAGAACG    1620

AACCAGGACG AAATAGACGA TCTGTTCAAT GCATTTGGAA GCAACTAACT GAGTCAACAT    1680

TTTGATCTAA ATCAATAATA AATAAGAAAA ACTTAGGATT AAAGAATCCT ATCATACCAG    1740

AACATAGAGT GGTAAATTTA GAGTCTGCTT GCAACTCAAT CAATAGAGAG TTGATCGAAA    1800

GCGATGCTAA AAACTATCAA ATCATGGATT CTTGGGAAGA GGAACCAAGA GATAAATCAA    1860

CTAATATCTC CTCGGCCCTC AACATCATTG AATTCATACT CAGCACCGAC CCCCAAGAAG    1920

ACCTATCGGA AAACGACACA ATCAACACAA GAACCCAGCA ACTCAGCGCC ACCATCTGTC    1980

AACCAGAAAT CAAACCAACA GAAACAAGTG AAAAAGTTAG TGGATCAACT GACAAAAATA    2040

GACAGTCTGG GTCATCACAC GAATGTACAA CAGAAGCAAA AGATAGAAAT ATTGATCAGG    2100

AAACTGTACA GGGAGGATCT GGGAGAAGAA GCAGCTCAGA TAGTAGAGCT GAGACTGTGG    2160

TCTCTGGAGG AATCTCTGGA AGCATCACAG ATTCTAAAAA TGGAACCCAA AACACGGAGA    2220

ATATTGATCT CAATGAAATT AGAAAGATGG ATAAGGACTC TATTGAGAGG AAAATGCGAC    2280

AATCTGCAGA TGTTCCAAGC GAGATATCAG GAAGTGATGT CATATTTACA ACAGAACAAA    2340

GTAGAAACAG TGATCATGGA AGAAGCTTGG AACCTATCAG TACACCTGAT ACAAGATCAA    2400

TGAGTGTTGT TACTGCTGCG ACACCAGATG ATGAAGAAGA AATACTAATG AAAAATAGTA    2460

GGATGAAGAA AAGTTCTTCA ACACACCAAG AAGATGACAA AGAATTAAA AAAGGGGGGG    2520

GGGGAAAAGG GAAAGACTGG TTTAAGAAAT CAAGAGATAC TGACAACCAG ACATCAACAT    2580

CAGATCACAA ACCCACATCA AAAGGGCAAA AGAAAATCTC AAAAACAACA ACCACCAACA    2640

CCGACACAAA GGGGCAAACA GAAACACAGA CAGAATCATC AGAAACACAA TCCCCATCAT    2700

GGAATCCCAT TATCGACAAC AACACTGACC GAACCGAACA GACAAGCACA ACCCCCCCAA    2760

CAACAACTCC CAGATCAACT CGTACAAAAG AATCAATCCG AACAAACTCT GAATCCAAAC    2820

CCAAGACACA AAAGACAATT GGAAAGGAAA GGAAGGATAC AGAAGAGAGC AATCGATTTA    2880

CAGAGAGGGC AATTACTCTA TTGCAGAATC TTGGTGTAAT TCAATCTACA TCAAAACTAG    2940

ATTTATATCA AGACAAACGA GTTGTATGTG TAGCAAATGT ACTAAACAAT GTAGATACTG    3000

CATCAAAGAT AGACTTCCTA GCAGGATTAG TCATAGGGGT TTCAATGGAC AATGACACAA    3060

AATTAATACA GATACAAAAT GAAATGTTAA ACCTCAAAGC AGATCTAAAG AGAATGGACG    3120

AATCACATAG AAGATTGATA GAAAATCAAA GAGAACAACT GTCATTGATC ACATCGTTAA    3180

TTTCAAATCT TAAAATTATG ACTGAGAGAG GAGGAAAGAA AGACCAAAAT GAATCCAATG    3240

AGAGAGTATC TATGATCAAG ACAAAATTGA AGAAGAAAA GATCAAGAAA ACCAGGTTTG    3300

ACCCACTTAT GGAGGCACAA GGTATTGACA AGAATATACC TGATCTATAT CGACATGCAG    3360

GAAATACGTT AGAGAACGAC GTACAAGTTA ATCAGAGAT ATTAAGTTCA TACAACGAGT    3420

CAAATGCAAC AAGACTAATA CCCAGAAAAG TGAGCAGTAC AATGAGATCA CTAGTTGCAG    3480

TCATCAACAA CAGCAATCTC CCACAAAGCA GAAAACAATC ATATATAAAC GAACTCAAAC    3540

ATTGCAAAAG TGATGAAGAA GTATCTGAAT TGATGGACAT GTTCAATGAA GATGTTAACA    3600

ATTGCTAAAG ATCAAATAAA AAAAACAACA CCGAATAAAT AGACAAGAAA CAACAGTAGA    3660

TCAAAACCTA TCAACACACA CAAAATCAAG CAGAGTGAAA CAATAGACAT CAATCAATAT    3720
```

```
ACAAATAAGA AAAATTTAGG ATTAAAGAAT AAATTAATCC TTGTCCAAAA TGAGTATAAC    3780

TAACTCTGCA ATATACACAT TCCCGGAGTC ATCATTCTCT GAGAATGGTC ATATAGAACC    3840

ATTACCACTC AAAGTCAATG AACAGAGAAA AGCAGTACCT CACATTAGAG TTGCCAAAAT    3900

CGGAAATCCA CCAAAACATG GATCCCGGTA TTTGGATGTC TTCTTACTCG GCTTCTTCGA    3960

GATGGAACGA ATCAAAGACA AATACGGGAG TGTGAATGAT CTTGACAGTG ACCCGGGTTA    4020

CAAAGTTTGT GGCTCTGGAT CATTACCAAT CGGATTAGCC AAATACACTG GAATGACCA     4080

GGAATTATTA CAACTAAACT GGACATAGAA CAGTCAAAGC GAAAGAAATG ATTGTTTATA    4140

CGGTACAAAA TATAAAACCA GAACTGTACC CATGGTCCAG TAGACTAAGA AAAGGAATGT    4200

TGTTCGATGC CAACAAAGTT GCTCTTGCTC CTCAATGTCT TCCACTAGAT AGGAGCATAA    4260

AATTCAGAGT AATCTTCGTT AATTGTACGG CAATTGGATC AATAACCTTG TTTAAAATTC    4320

CCAAGTCAAT GGCATCACTA TCTCTACCCA GCACAATATC AATCAATCTG CAGGTACACA    4380

TCAAAACAGG GGTTCAGACT GATTCTAAAG GGATAGTTCA AATTTTGGAT GAGAAGGGTG    4440

AAAAATCACT GAATTTCATG GTCCATCTCG GATTGATCAA AAGAAAAGTA GGCAGAATGT    4500

ACTCTGTCGA GTACTGTAAA CAGAAAATCG AGAAATGAG ATTGATATTT TCTTTGGGAT     4560

TAGTTGGAGG AATCAGTCTT CATGTCAATG CAACTGGATC TATATCAAAA ACACTAGCAA    4620

GTCAGCTGGT ATTCAAAAGG GAGATTTGTT ATCCCTTAAT GGATCTAAAT CCACATCTCA    4680

ATCTAGTTAT CTGGGCTTCA TCAGTAGAGA TTACAAGAGT GGATGCAATT TTCCAACCTT    4740

CTTTACCTGG CGAGTTCAGA TACTATCCTA ACATTATTGC AAAAGGAGTT GGGAAAATCA    4800

AACAATGGAA CTAGTAATCT CTATTTTGAT CTGGATATAT CTATTAAGCC AAAGCAAATA    4860

AGAGATAATC AAAAACTTAG GACAAAAGAA GTCAATACCA CAACTATTA GCAGCCACAC     4920

TCGCTGGAAC AAGAAAGAAG GGATAAAAAA AGTTTAACAG AAGAAACAAA AACAAAAAGC    4980

ACAGAACACC AGAACAACAA GATCAAAACA CCCAACCCAC TCAAAACGAA AATCTCAAAA    5040

GAGATTGGCA ACACAACAAA CACTGAACAT CATGCCAACC TCAATACTGC TAATTATTAC    5100

AACCATGATT ATGGCATCTT TCTGCCAAAT AGATATCACA AAACTACAGC ATGTAGGTGT    5160

ATTGGTTAAC AGTCCCAAAG GGATGAAGAT ATCACAAAAC TTTGAAACAA GATATCTAAT    5220

TTTGAGCCTC ATACCAAAAA TAGAAGATTC TAACTCTTGT GGTGACCAAC AGATCAAGCA    5280

ATACAAGAGG TTATTGGATA GACTGATCAT TCCTTTATAT GATGGATTAA GATTACAGAA    5340

GGATGTGATA GTGTCCAATC AAGAATCCAA TGAAAACACT GACCCCAGAA CAAAACGATT    5400

CTTTGGAGGG GTAATTGGAA CTATTGCTCT GGGAGTGGCA ACCTCAGCAC AAATTACAGC    5460

GGCAGTTGCT CTGGTTGAAG CCAAGCAGGC AAGATCAGAC ATTGAAAAAC TCAAGGAAGC    5520

AATCAGGGAC ACAAACAAAG CAGTGCAGTC AGTCCAGAGC TCCATAGGAA ATTTGATAGT    5580

AGCAATTAAA TCGGTCCAGG ATTATGTCAA CAAAGAAATC GTGCCATCAA TTGCGAGATT    5640

AGGTTGTGAA GCAGCAGGAC TTCAGTTAGG AATTGCATTA ACACAGCATT ACTCAGAATT    5700

AACAAACATA TTCGGTGATA ACATAGGATC ATTACAAGAA AAAGGGATAA AATTACAAGG    5760

TATAGCATCA TTATACCGCA CAAATATCAC AGAGATATTC ACAACATCAA CAGTTGATAA    5820

ATATGATATT TATGATCTAT TATTTACAGA ATCAATAAAG GTGAGAGTTA TAGATGTTGA    5880

CTTGAATGAT TACTCAATCA CCCTCCAAGT CAGACTCCCT TTATTAACTA GACTGCTGAA    5940

CACCCAGATT TACAGAGTAG ATTCCATATC ATATAACATC AAAACAGAG AATGGTATAT     6000

CCCTCTTCCC AGCCACATCA TGACAAAAGG GGCATTTCTA GGTGGAGCAG ATGTCAAAGA    6060
```

```
ATGTATAGAA GCATTCAGCA GTTATATATG CCCTTCTGAT CCAGGATTTG TACTAAACCA    6120
TGAAATGGAG AGCTGTTTAT CAGGAAACAT ATCCCAATGT CCAAGAACCG TGGTTAAATC    6180
AGACATTGTT CCAAGATATG CATTTGTCAA TGGAGGAGTG GTTGCAAATT GTATAACAAC    6240
CACATGTACA TGCAACGGTA TCGGTAATAG AATCAATCAA CCACCTGATC AAGGAGTAAA    6300
AATTATAACA CATAAAGAAT GTAATACAAT AGGTATCAAC GGAATGCTGT TCAATACAAA    6360
TAAAGAAGGA ACTCTTGCAT TTTACACACC AAATGATATA ACATTAAACA ATTCTGTTGC    6420
ACTTGATCCA ATTGACATAT CAATCGAGCT CAATAAGGCC AAATCAGATC TAGAAGAGTC    6480
AAAAGAATGG ATAAGAAGGT CAAATCAAAA ACTAGATTCC ATTGGAAATT GGCATCAATC    6540
TAGCACCACA ATCATAATTG TTTTGATAAT GATAATTATA TTGTTTATAA TTAATGTAAC    6600
GATAATTATA ATTGCAGTTA AGTATTACAG AATTCAAAAG AGAAATCGAG TGGATCAAAA    6660
TGATAAACCA TATGTATTAA CAAACAAATG ACAGATCTAT AGATCATTAG ATATTAAAAT    6720
TATAAAAAAC TTAGGAGTAA AGTTACGCAA TTCAACTCTA CTCATATAAT TGAGAAAGAA    6780
CCCAACAGAC AAATCCAAAT CCGAGATGGA ATACTGGAAG CACACCAATC ACGGGAAAGA    6840
TGCTGGTAAT GAGCTGGAAA CATCCATGGC TACTCATGGC AACAAGATCA CCAACAAGAT    6900
AACATATATA TTATGGACAA TAATCCTGGT GTTATTATCA ATAGTCTTCA TCATAGTGCT    6960
AATTAATTCC ATCAAAAGTG AAAAAGCCCA TGAATCATTG CTACAAGACG TAAACAATGA    7020
GTTTATGGAA GTTACAGAAA AGATCCAAAT GGCATCGGAT AATATTAATG ATCTAATACA    7080
GTCAGGAGTG AATACAAGGC TTCTTACAAT TCAGAGTCAT GTCCAGAATT ATATACCGAT    7140
ATCATTGACA CAACAAATGT CGGATCTTAG GAAATTCATT AGTGAAATTA CAATTAGGAA    7200
TGATAATCGA GAAGTGCCTC CACAAAGAAT AACACATGAT GCGGGCATAA AACCTTTAAA    7260
TCCAGATGAT TTTTGGAGAT GCACGTCTGG TCTTCCATCT TTAATGAAAA CTCCAAAAAT    7320
AAGGTTAATG CCGGGGCCGG GATTATTAGC TATGCCAACG ACTGTTGATG GCTGTGTTAG    7380
AACTCCGTCC TTAGTTATTA ATGATCTGAT TTATGCTTAT ACCTCAAATC TAATTACTCG    7440
AGGTTGCCAG GATATAGGAA AATCATATCA AGTATTACAG ATAGGGATAA TAACTGTAAA    7500
CTCAGACTTG GTACCTGACT TAAATCCTAG GATCTCTCAT ACTTTCAACA TAAATGACAA    7560
TAGAAAGTCA TGTTCTCTAG CACTCCTAAA CACAGATGTA TATCAACTGT GTTCGACTCC    7620
CAAAGTTGAT GAAAGATCAG ATTATGCATC ATCAGGCATA GAAGATATTG TACTTGATAT    7680
CGTCAATCAT GATGGTTCAA TCTCAACAAC AAGATTTAAG AACAATAATA TAAGTTTTGA    7740
TCAACCATAT GCGGCATTAT ACCCATCTGT TGGACCAGGG ATATACTACA AAGGCAAAAT    7800
AATATTTCTC GGGTATGGAG GTCTTGAACA TCCAATAAAT GAGAATGCAA TCTGCAACAC    7860
AACTGGGTGT CCCGGGAAAA CGCAGAGAGA CTGCAATCAG GCATCTCATA GTCCTTGGTT    7920
TTCAGACAGA AGGATGGTCA ACTCCATTAT TGTTGTTGAC AAGGGCTTAA ACTCAATTCC    7980
AAAGCTGAAG GTATGGACGA TATCCATGAG ACAAAATTAC TGGGGGTCAG AAGGAAGGCT    8040
ACTTCTACTA GGTAACAAGA TCTATATATA TACAAGATCT ACAAGTTGGC ATAGCAAGTT    8100
ACAATTAGGA ATAATTGATA TTACTGATTA CAGTGATATA AGAATAAAAT GGACATGGCA    8160
TAATGTGCTA TCAAGACCAG GAAACAATGA ATGTCCATGG GGACATTCAT GCCCAGATGG    8220
ATGTATAACA GGAGTATATA CTGATGCATA TCCACTCAAT CCCACAGGGA GCATTGTGTC    8280
ATCTGTCATA TTAGACTCGC AAAAATCGAG AGTAAACCCA GTCATAACTT ACTCAACATC    8340
AACTGAAAGG GTAAACGAGC TGGCCATCCG AAACAAAACA CTCTCAGCTG GATATACAAC    8400
AACGAGCTGC ATTACACACT ATAACAAAGG ATATTGTTTT CATATAGTAG AAATAAATCA    8460
```

-continued

```
TAAAAGCTTA GACACATTCC AACCTATGTT GTTCAAAACA GAGATTCCAA AAAGCTGCAG    8520

TTAATCATAA TTAACCATAA TATGTATTAA CCTATCTATA ATACAAGTAT ATGATAAGTA    8580

ATCAGCAATC AGACAATAGA TAAAAGAGAA ATATAAAAAA CTTAGGAGCA AAGCATGCTC    8640

GAAAAATGGA CACTGAATCT AACAATGGCA CTGTATCTGA CATACTCTAT CCTGAGTGTC    8700

ACCTTAATTC TCCTATCGTT AAGGGTAAAA TAGCACAATT ACACACTATT ATGAGTCTAC    8760

CACAGCCTTA CGATATGGAT GACGACTCAA TACTAGTTAT CACTAGACAG AAAATAAAAC    8820

TCAATAAATT AGATAAAAGA CAACGATCTA TTAGAAGATT AAAATTAATA TTAACTGAGA    8880

AAGTGAATGA CTTAGGAAAA TACACATTTA TTAGATATCC AGAAATGTCA AAAGAAATGT    8940

TCAAATTACA TATACCTGGT ATTAACAGTA AAGTGACTGA ATTATTACTT AAAGCAGATA    9000

GAACATATAG TCAAATGACT GATGGATTAA GAGATCTATG GATTAATGTG CTATCGAAAT    9060

TAGCCTCAAA AAATGATGGA AGCAATTATG ATCTTAATGA AGAAATTAAT AATATATCAA    9120

AAGTTCACAC AACCTATAAA TCAGATAAAT GGTATAATCC ATTCAAAACA TGGTTCACTA    9180

TCAAGTATGA TATGAGAAGA TTGCAAAAAG CTCGAAATGA GGTCACTTTT AATATGGGGA    9240

AAGATTATAA CTTGTTAGAA GACCAGAAGA ATTTCTTATT GATACATCCA GAATTGGTTT    9300

TAATATTAGA TAAACAAAAC TATAATGGTT ATCTAATTAC TCCTGAATTA GTATTGCCGT    9360

ATTGTGACGT AGTTGAAGGC CGATGGAATA TAAGTGCATG TGCTAAGTTA GATCCAAAAT    9420

TACAATCTAT GTATCAGAAA GGCAATAATC TGTGGGAAGT GATAGATAAA TTGTTTCCAA    9480

TTATGGGAGA AAAGACATTT GATGTGATAT CATTATTAGA ACCACTTGCA TTATCTCTAA    9540

TTCAAACTCA TGATCCTGTT AAACAATTAA GGGGAGCTTT TTTAAATCAT GTGTTATCCG    9600

AGATGGAATT GATATTTGAA TCTAGAGAAT CGATTAAAGA ATTTCTGAGT GTAGATTACA    9660

TTGATAAAAT CTTAGATATA TTTAATAAAT CTACAATAGA TGAAATAGCA GAGATTTTCT    9720

CTTTTTTTAG AACATTTGGG CATCCTCCAT TAGAGGCTAG TATTGCAGCA GAAAAAGTTA    9780

GAAAATATAT GTATATTGGG AAACAATTAA AATTTGACAC TATTAATAAA TGTCATGCTA    9840

TCTTCTGTAC AATAATAATT AACGGATATA GAGAAAGGCA TGGTGGACAG TGGCCTCCTG    9900

TGACATTACC TGATCATGCA CACGAATTCA TCATAAATGC TTACGGTTCA AATTCTGCGA    9960

TATCATATGA AAACGCTGTT GATTATTACC AGAGCTTTAT AGGAATAAAA TTTAATAAAT   10020

TCATAGAACC TCAGTTAGAT GAAGATTTGA CAATTTATAT GAAAGATAAA GCATTGTCTC   10080

CAAAAAAATC AAACTGGGAC ACAGTTTCTC CTGCATCTAA TTTACTGTAC CGTACTAACG   10140

CATCCAACGA ATCACGAAGA TTAGTTGAAA AATTTATAGC AGATAGTAAA TTTGATCCTA   10200

ATCAGATATT AGATTATGTA GAATCTGGGG ACTGGTTAGA TGATCCAGAA TTTAATATTT   10260

CTTATAGTCT TAAAGAAAAA GAGATCAAAC AAGAAGGTAG ACTCTTTGCA AAAATGACAT   10320

ATAAAATGAG AGCTACACAA GTTTTATCAG AGACACTACT TGCAAATAAT ATAGGGAAAT   10380

TCTTTCAAGA AAATGGGATG GTAAAAGGAG AGATTGAATT ACTTAAGAGA TTAACAACCA   10440

TATCAATATC AGGAGTTCCA CGGTATAATG AAGTATACAA TAATTCTAAA AGTCATACAG   10500

ATGATCTTAA AACCTACAAT AAAATAAGTA ATCTCAATTT GTCTTCTAAT CAGAAATCAA   10560

AGAAATTTGA ATTCAAGTCA ACGGATATTT ACAATGATGG ATACGAGACT GTGAGCTGTT   10620

TTCTAACAAC AGATCTCAAA AAATACTGTC TTAATTGGAG ATATGAATCA ACAGCTCTAT   10680

TTGGAGAAAC TTGCAACCAA ATATTTGGAT TAAATAAATT GTTTAATTGG TTACACCCTC   10740

GTCTTGAAGG AAGTACAATC TATGTAGGTG ATCCCTATTG TCCTCCATCA GATAAGGAAC   10800
```

```
ATATATCATT AGAGGATCAC CCTGATTCTG GATTTTATGT TCATAACCCA AGAGGGGGTA    10860

TAGAAGGATT TTGTCAAAAA TTGTGGACAC TCATATCTAT AAGTGCAATA CATCTAGCAG    10920

CTGTTAGAAT AGGCGTAAGG GTAACTGCAA TGGTTCAAGG AGATAATCAA GCTATAGCTG    10980

TAACAACAAG AGTACCCAAC AATTATGACT ACAGAGTTAA GAAGGAGATA GTTTATAAAG    11040

ATGTGGTGAG ATTTTTTGAT TCATTAAGAG AAGTAATGGA TGATCTAGGT CATGAACTTA    11100

AATTAAATGA AACAATTATA AGTAGCAAGA TGTTCATATA TAGCAAAAGA ATATATTACG    11160

ATGGGAGAAT TCTTCCCCAA GCTCTGAAAG CATTATCTAG ATGTGTCTTC TGGTCAGAGA    11220

CAGTAATAGA CGAAACAAGA TCAGCATCTT CAAACTTGGC AACATCATTT GCAAAAGCAA    11280

TTGAGAATGG TTATTCACCT GTTCTAGGAT ATGCATGCTC AATTTTTAAG AACATTCAAC    11340

AACTATATAT TGCCCTTGGG ATGAATATCA ATCCAACTAT AACACAGAAT ATCAAAGATT    11400

TATATTTTAG GAATCCAAAT TGGATGCAAT ATGCATCTTT AATACCTGCT AGTGTTGGGG    11460

GATTCAATTA CATGGCCATG TCAAGATGTT TTGTAAGGAA TATTGGCGAT CCATCAGTTG    11520

CCGCATTAGC TGATATTAAA AGATTTATTA AGGCGAACCT ATTAGACCGA AGTGTTCTTT    11580

ATAGGATTAT GAATCAAGAA CCAGGTGAGT CATCTTTTTT GGACTGGGCT TCAGACCCAT    11640

ATTCATGCAA TTTACCACAA TCTCAAAATA TAACCACTAT GATAAAAAAT ATAACAGCAA    11700

GAAATGTATT ACAAGATTCA CCGAATCCAT TATTATCTGG ATTATTCACA AATACAATGA    11760

TAGAAGAAGA TGAAGAATTA GCTGAGTTCT TGATGGACAG GAAGGTAATT CTCCCTAGAG    11820

TTGCACATGA TATTCTAGAT AATTCTCTCA CAGGAATCAG AAATGCTATA GCTGGAATGT    11880

TAGATACGAC AAAATCTCTA ATTCGGGTTG GCATAAATAG AGGAGGACTG ACATACAGTT    11940

TGTTGAGGAA AATCAGTAAT TACGATCTAG TACAATATGA AACACTAAGT AGGACTTTGC    12000

GACTAATTGT AAGCGATAAA ATCAGGTATG AAGATATGTG TTCGGTAGAC CTTGCTATAG    12060

CATTGCGTCA AAAGATGTGG ATTCATTTAT CAGGAGGAAG GATGATAAGT GGACTTGAAA    12120

CACCTGATCC ATTAGAATTA CTATCTGGGG TGATAATAAC AGGATCGGAA CATTGTAAAA    12180

TATGTTATTC TTCAGATGGC ACAAACCCAT ATACTTGGAT GTATTTACCG GGTAATATTA    12240

AAATAGGATC AGCAGAAACA GGTATATCAT CATTGAGAGT TCCTTATTTT GGATCAGTCA    12300

CTGATGAGAG ATCTGAGGCA CAATTGGGAT ATATCAAGAA TCTTAGTAAA CCTGCAAAAG    12360

CCGCAATAAG AATAGCAATG ATATATACAT GGGCATTTGG TAATGATGAG ATATCTTGGA    12420

TGGAGGCCTC ACAAATAGCA CAAACACGTG CAAATTTTAC ACTAGATAGT CTCAAAATTC    12480

TAACACCGGT AGCTACATCA ACAAATTTAT CACACAGATT AAAGGATACT GCAACCCAGA    12540

TGAAGTTCTC CAGTACATCA TTGATTAGGG TCAGCAGATT CATAACAATG TCCAATGATA    12600

ACATGTCTAT CAAGGAAGCT AATGAGACCA AGATACCAA TCTTATTTAT CAACAAATAA    12660

TGTTAACAGG ATTAAGTGTT TTCGAATATT TATTTAGATT AGAAGAAACC ACAGGACACA    12720

ACCCCATAGT TATGCATCTG CACATAGAAG ATGAGTGTTG TATTAAAGAA AGTTTTAATG    12780

ATGAGCATAT TAATCCAGAG TCTACATTAG AATTAATTAG GTACCCTGAA AGTAATGAAT    12840

TTATTTATGA TAAAGACCCG CTCAAGGACG TGGACTTATC AAAACTTATG GTTATTAAAG    12900

ATCATTCTTA CACAATTGAT ATGAATTATT GGGATGATAC TGACATCATA CATGCAATTT    12960

CAATATGTAC TGCAATTACA ATAGCAGACA CTATGTCACA ATTAGATCGA GATAACTTAA    13020

AAGAGATAAT AGTCATTGCA AATGATGATG ATATTAATAG CTTAATCACT GAATTTTTGA    13080

CTCTTGATAT ACTTGTATTT CTTAAGACAT TTGGTGGATT ATTAGTAAAT CAATTTGCAT    13140

ACACTCTTTA TAGTTTAAAA ACCGAAGGTA GGGACCTCAT TTGGGATTAT ATAATGAGAA    13200
```

```
CACTGAGAGA TACTTCCCAT TCAATATTAA AAGTATTATC TAATGCATTA TCTCATCCTA    13260

AAGTATTCAA GAGGTTCTGG GATTGTGGAG TCTTAAACCC TATTTATGGC CCTAATACTG    13320

CTAGTCAAGA CCAGATAAAA CTTGCCCTCT CTATATGTGA ATATTCACTA GATCTATTTA    13380

TGAGAGAATG GTTGAATGGT GTATCACTTG AAATATACAT TTGTGACAGC GATATGGAAG    13440

TTGCGAATGA TAGGAAACAA GCCTTTATTT CTAGACACCT TTCATTTGTT TGTTGTTTAG    13500

CAGAAATTGC ATCTTTTGGA CCTAACCTGT TAAACTTAAC ATACTTAGAG AGACTTGATC    13560

TATTGAAACA ATATCTTGAA TTAAATATTA AAGACGACCC TACTCTTAAA TATGTACAAA    13620

TATCTGGATT ATTAATTAAA TCGTTCCCAT CAACTGTAAC ATACGTAAGA AAGACTGCAA    13680

TCAAATATTT AAGGATTCGT GGTATTAGTC CACCTGAGGT AATTGATGAT TGGGATCCGA    13740

TAGAAGATGA AAATATGCTG GATAACATTG TCAAAACTAT AAATGATAAT TGTAATAAAG    13800

ATAATAAAGG GAATAAAATT AACAATTTCT GGGGACTAGC GCTTAAGAAC TATCAGGTCC    13860

TTAAAATCAG ATCTATAACA AGTGATTCTG ATAATAATGA TAGATCAGAT GCTAGTACCG    13920

GTGGTTTGAC ACTTCCTCAA GGGGGGAATT ATCTATCACA TCAATTGAGA TTATTCGGAA    13980

TCAACAGCAC TAGTTGTCTG AAAGCTCTTG AGTTATCACA AATTTTAATG AAGGAAGTTA    14040

ATAAAGACCA GGACAGGCTC TTCCTAGGAG AAGGAGCAGG AGCTATGCTA GCATGTTATG    14100

ATGCCACATT AGGACCTGCA ATTAATTATT ATAATTCCGG TTTGAATATA ACAGATGTAA    14160

TTGGTCAACG AGAATTGAAA ATATTCCCTT CAGAGGTATC ATTAGTAGGT AAAAAATTAG    14220

GAAATGTGAC ACAGATCCTT AATAGGGTAA AAGTACTGTT CAATGGAAAT CCAAATTCAA    14280

CATGGATAGG AAATATGGAA TGCGAGACGT TAATATGGAG TGAATTGAAT GATAAGTCTA    14340

TTGGATTGGT ACATTGTGAT ATGGAAGGAG CTATCGGTAA ATCAGAAGAA ACTGTTCTAC    14400

ATGAACACTA TAGTGTTATA AGAATTACAT ACTTGATTGG GGATGATGAT GTTGTTTTAA    14460

TTTCCAAAAT TATACCTACA ATCACTCCGA ATTGGTCTAG AATACTTTAT CTATATAAGT    14520

TATATTGGAA AGATGTAAGT ATAATATCAC TTAAAACTTC TAATCCTGCA TCAACAGAAT    14580

TATATCTAAT TTCAAAAGAT GCGTATTGTA CTATAATGGA ACCTAGTGAA GTTGTTTTAT    14640

CAAAACTTAA AAGATTGTCA CTCTTGGAAG AAAATAATCT ATTAAAATGG ATCATTTTAT    14700

CAAAGAAGAA AAATAATGAA TGGTTACATC ATGAAATCAA AGAAGGGGAA AGAGATTATG    14760

GAGTTATGAG ACCATATCAT ATGGCATTAC AAATTTTTGG ATTTCAAATC AATTTAAATC    14820

ATCTGGCGAA AGAATTTTTA TCAACTCCAG ATCTGACTAA TATCAACAAT ATAATCCAAA    14880

GTTTTCAGAG AACAATCAAG GATGTTTTGT TTGAATGGAT TAATATAACT CATGATGGTA    14940

AGAGACATAA ATTAGGCGGG AGATATAACA TATTCCCACT GAAAAATAAG GGGAAATTAA    15000

GACTGCTATC GAGAAGACTA GTATTAAGTT GGATTTCATT GTCATTATCG ACTCGATTAC    15060

TTACAGGTCG TTTTCCTGAT GAAAAATTTG AACATAGAGC ACAGACTGGA TATGTGTCAT    15120

TACCTGATAC TGATTTAGAA TCATTAAAGT TATTGTCGAA AAACACCATT AAGAATTACA    15180

GAGAGTGTAT AGGGTCAATA TCATATTGGT TTCTAACCAA AGAAGTTAAA ATACTTATGA    15240

AATTGATTGG TGGTGCTAAA TTATTAGGAA TTCCCAGACA ATATAAGGAA CCCGAAGAAC    15300

AGTTATTAGA AGACTACAAT CAACATGATG AATTTGATAT AGATTAAAAT ACAAATACAA    15360

TAAAGATATA TCCTAACCTT TATCATTAAG CCTAAAGATA GACAAAAAGT AAGAAAAACA    15420

TGTAATATAT ATATACCAAA CAGAGTTCTT CTCTTGTTTG GT                      15462
```

(2) INFORMATION FOR SEQ ID NO:2:

```
        (i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

TAGTCGGCCC TAATACGACT CACTATAGGA CCAAACAAGA GAAGAAACT              49

(2) INFORMATION FOR SEQ ID NO:3:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GAAATTATAG AGCTCCCTTT TCT                                         23

(2) INFORMATION FOR SEQ ID NO:4:

(i) SEQUENCE CHARACTERISTICS:
            (A) LENGTH: 95 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

TAAGGCCTAA AGATAGACAA AAACTAAGAA AAACATGTAA TATATATATA CCAAACAGAG  60

TTCTTCTCTT GTTTGGTGGG TCGGCATGGC ATCTC                            95

(2) INFORMATION FOR SEQ ID NO:5:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

CTGGGTACCT CCCTTAGCCA TCCGAGT                                     27
```